(12) United States Patent
Chen et al.

(10) Patent No.: US 10,888,323 B2
(45) Date of Patent: Jan. 12, 2021

(54) STAPLE CARTRIDGE ASSEMBLY AND MEDICAL STAPLER USING THE STAPLE CARTRIDGE ASSEMBLY

(71) Applicant: TOUCHSTONE INTERNATIONAL MEDICAL SCIENCE CO., LTD., Suzhou (CN)

(72) Inventors: Wangdong Chen, Suzhou (CN); Yanping Ye, Suzhou (CN)

(73) Assignee: TOUCHSTONE INTERNATIONAL MEDICAL SCIENCE CO., LTD., Suzhou (CN)

( * ) Notice: Subject to any disclaimer, the term of this patent is extended or adjusted under 35 U.S.C. 154(b) by 421 days.

(21) Appl. No.: 15/540,975

(22) PCT Filed: Dec. 22, 2015

(86) PCT No.: PCT/CN2015/098181
§ 371 (c)(1),
(2) Date: Jun. 29, 2017

(87) PCT Pub. No.: WO2016/107450
PCT Pub. Date: Jul. 7, 2016

(65) Prior Publication Data
US 2017/0340328 A1 Nov. 30, 2017

(30) Foreign Application Priority Data

Dec. 31, 2014 (CN) .......................... 2014 1 0845676
Dec. 31, 2014 (CN) .......................... 2014 1 0850323

(51) Int. Cl.
*A61B 17/072* (2006.01)
*A61B 17/064* (2006.01)
(Continued)

(52) U.S. Cl.
CPC ...... *A61B 17/07207* (2013.01); *A61B 17/064* (2013.01); *A61B 17/1155* (2013.01);
(Continued)

(58) Field of Classification Search
CPC .. A61B 2017/2936; A61B 2017/07235; A61B 2017/2933; A61B 2017/07271;
(Continued)

(56) References Cited

U.S. PATENT DOCUMENTS 5,040,715 A * 8/1991 Green .............. A61B 17/07207
227/176.1
5,478,003 A * 12/1995 Green .............. A61B 17/07207
227/176.1
(Continued)

FOREIGN PATENT DOCUMENTS

CN 101156792 A 4/2008
CN 101507633 A 8/2009
(Continued)

OTHER PUBLICATIONS

International Search Report, dated Mar. 16, 2016, for International Application No. PCT/CN2015/098181, 5 Pages.

*Primary Examiner* — Thomas M Wittenschlaeger
(74) *Attorney, Agent, or Firm* — Seed IP Law Group LLP

(57) ABSTRACT

A staple cartridge assembly comprises a staple cartridge, an anvil and a cutter, wherein the cutter comprises a first end and a second end; the staple cartridge assembly also comprises a rotation shaft and an auxiliary closing member which is connected with the rotation shaft; the staple cartridge assembly is also provided with a driving component capable of driving the rotation shaft to rotate; the driving component drives the rotation shaft to drive the auxiliary closing member to move in the process in which the staple cartridge assembly is converted from an original status to a
(Continued)

closed status; when at least the staple cartridge assembly is in the closed status, one end surface of the auxiliary closing member abuts against the anvil to apply a force to the anvil for driving the anvil to be closed towards the staple cartridge.

20 Claims, 22 Drawing Sheets

(51) Int. Cl.
*A61B 17/115* (2006.01)
*A61B 17/29* (2006.01)

(52) U.S. Cl.
CPC ............... *A61B 2017/07235* (2013.01); *A61B 2017/07271* (2013.01); *A61B 2017/07285* (2013.01); *A61B 2017/2933* (2013.01); *A61B 2017/2936* (2013.01)

(58) Field of Classification Search
CPC ...... A61B 2017/07285; A61B 17/1155; A61B 17/07207; A61B 17/064
See application file for complete search history.

(56) References Cited

U.S. PATENT DOCUMENTS

| | | | | |
|---|---|---|---|---|
| 5,779,132 A | * | 7/1998 | Knodel | A61B 17/07207 227/176.1 |
| 5,816,471 A | * | 10/1998 | Plyley | A61B 17/064 227/178.1 |
| 7,434,717 B2 | * | 10/2008 | Shelton, IV | A61B 17/105 227/176.1 |
| 7,546,940 B2 | * | 6/2009 | Milliman | A61B 17/115 227/175.1 |
| 7,959,051 B2 | * | 6/2011 | Smith | A61B 17/07207 227/176.1 |
| 2004/0232199 A1 | * | 11/2004 | Shelton, IV | A61B 17/07207 227/175.2 |
| 2008/0078805 A1 | * | 4/2008 | Omaits | A61B 17/064 227/176.1 |
| 2014/0239047 A1 | | 8/2014 | Hodgkinson et al. | |
| 2014/0263550 A1 | * | 9/2014 | Aranyi | A61B 17/07207 227/175.3 |
| 2016/0174975 A1 | * | 6/2016 | Shelton, IV | A61B 17/07207 227/175.1 |

FOREIGN PATENT DOCUMENTS

| | | |
|---|---|---|
| CN | 202982103 U | 6/2013 |
| CN | 2 764 837 A1 | 8/2014 |
| CN | 104042276 A | 9/2014 |
| CN | 104490438 A | 4/2015 |
| CN | 204364052 U | 6/2015 |
| CN | 204379344 U | 6/2015 |

* cited by examiner

STAPLE CARTRIDGE ASSEMBLY AND MEDICAL STAPLER USING THE STAPLE CARTRIDGE ASSEMBLY

This application claims the priority of the Chinese patent application No. 201410845676.0, filed on Dec. 31, 2014 and titled "staple cartridge assembly and medical stapler using the staple cartridge assembly", and also claims the priority of the Chinese patent application No. 201410850323.X, filed on Dec. 31, 2014 and titled "staple assembly and endoscopic cutting stapler using the staple assembly", which are incorporated herein by reference in their entirety.

TECHNICAL FIELD

The present invention is related to the technical field of medical instruments, and more particularly, to a staple cartridge assembly and a medical stapler using the staple cartridge assembly.

BACKGROUND

A medical stapler is a common medical instrument when performing surgeries to physiological tissues such as intestinal tissues. It is a medical device replacing traditional manual suture. With development of modern technologies and improvement of manufacturing techniques, current medical staplers used clinically are reliable in quality, convenient in use and appropriate tightness and tension. They have the advantages of quick suture, simple operation and less side effects and surgical complications. Sometimes, they can cut tumor tissues which could not be removed in past surgeries, so they are praised highly by foreign and domestic surgeons. The difference in performance of such instruments plays a crucially important role in the whole surgical effect.

A staple cartridge and an anvil of the medical stapler are connected to form a clamp structure. In a surgery, jaws of the clamp formed by the staple cartridge and the anvil are opened first to clamp the physiological tissues, and are then closed to each other, such that the physiological tissues are sutured and cut. When relatively thicker physiological tissues are clamped, the jaws are closed with greater resistance, which will give the anvil and the staple cartridge a large opening reaction force during cutting and suture, easily resulting in breakage of the cutter. At the same time, the clamping effect of the anvil and the staple cartridge on the tissues becomes weak, and physiological tissues to be sutured are also easy to be disengaged from the anvil and the staple cartridge, which not only brings inconvenience to the operation of the doctor, but also brings greater risks to the surgery.

SUMMARY

The objectives of the present invention are to provide a staple cartridge assembly and a medical stapler using the staple cartridge assembly.

To realize one of the above objectives, an embodiment of the present invention provides a staple cartridge assembly. The staple cartridge assembly comprises a staple cartridge, an anvil and a cutter, wherein the cutter comprises a first end and a second; the staple cartridge assembly also comprises a rotation shaft and an auxiliary closing member which is connected with the rotation shaft; wherein the staple cartridge assembly is also provided with a driving component capable of driving the rotation shaft to rotate; the driving component drives the rotation shaft to drive the auxiliary closing member to move in the process in which the staple cartridge assembly is converted from an original status to a closed status; when at least the staple cartridge assembly is in the closed status, one end surface of the auxiliary closing member abuts against the anvil to apply a force to the anvil for driving the anvil to be closed towards the staple cartridge.

As an improvement of the embodiment of the present invention, the auxiliary closing member includes a cam rotatable around an axis of the rotation shaft; and the driving component drives the rotation shaft to drive the cam to rotate in the process in which the staple cartridge assembly is converted from the original status to the closed status; when at least the staple cartridge assembly is in the closed status, a cam surface of the cam abuts against the anvil to apply a force to the anvil for driving the anvil to be closed towards the staple cartridge.

As another improvement of the embodiment of the present invention, during a process of firing the staple cartridge assembly, the force is always applied to the anvil.

As yet another improvement of the embodiment of the present invention, during the process of firing the staple cartridge assembly, the cutter moves towards a distal end of the staple cartridge assembly, and the driving component is detached from the rotation shaft and maintains to be stationary after the driving component is detached from the rotation shaft.

As yet another improvement of the embodiment of the present invention, during a process of returning to the original status of the staple cartridge assembly after being fired, the cutter moves from a distal end of the staple cartridge assembly towards the proximal end thereof, and the driving component drives the rotation shaft to drive the cam to rotate such that the cam surface is detached from the anvil.

As yet another improvement of the embodiment of the present invention, the driving component includes a first driving surface and a second driving surface; during the process in which the staple cartridge assembly is converted from the original status to the closed status, the first driving surface drives the rotation shaft to rotate in a first direction; during a process of returning to the original status of the staple cartridge assembly after being fired, the second driving surface drives the rotation shaft to rotate in a second direction which is opposite to the first direction.

As yet another improvement of the embodiment of the present invention, the rotation shaft includes a concave portion, a contact portion and a convex portion; in the process in which the staple cartridge assembly is converted from the original status to the closed status, the first driving surface gradually approaches and contacts the contact portion to drive the rotation shaft to rotate in the first direction; in a firing process of the staple cartridge assembly, the driving component is detached from the rotation shaft; during a process of returning to the original status of the staple cartridge assembly after being fired, the second driving surface gradually approaches and contacts the convex portion to drive the rotation shaft to rotate in the second direction.

As yet another improvement of the embodiment of the present invention, the staple cartridge assembly further comprises a staple cartridge bracket, a connector and an adapter, wherein the staple cartridge detachably connects the staple cartridge bracket, the connector is located at a proximal end of the staple cartridge bracket, and the adapter is connected to the connector and the staple cartridge bracket; and wherein the adapter cooperates with the staple cartridge bracket to form an accommodating space in which the rotation shaft can rotate, in which at least part of the rotation shaft is arranged and which limits the rotation shaft.

As yet another improvement of the embodiment of the present invention, the adapter includes a fixing portion to cooperate with the staple cartridge bracket; an end surface of the fixing portion close to the staple cartridge bracket is arranged as a first arced surface; a protrusion corresponding to the fixing portion extends on the staple cartridge bracket; an end surface of the protrusion close to the fixing portion is arranged as a second arced surface; and the first and second arced surfaces together define the accommodating space.

As yet another improvement of the embodiment of the present invention, the anvil includes a cutter receiving groove to allow the cutter to pass; and the staple cartridge assembly includes two cams located at both sides of the cutting part of the cutter respectively and capable of contacting the anvil at both sides of the cutter receiving groove respectively.

As yet another improvement of the embodiment of the present invention, the staple cartridge assembly further comprises a staple cartridge bracket for detachably accommodating the staple cartridge; and a cutter push rod for driving the cutter to move, wherein the auxiliary closing member is movably arranged in the staple cartridge bracket, and includes a sliding block and a connecting rod; the rotation shaft is pivotally connected to the staple cartridge bracket, and is rotatable relative thereto; two ends of the connecting rod are pivotally connected to the sliding block and the rotation shaft respectively; when the cutter push rod drives the cutter to move towards the distal end, the driving component drives the rotation shaft to rotate and drives the sliding block via the connecting rod, such that the sliding block moves to a position below a proximal end of the anvil; when the cutter moves to the proximal end to return to its original position, the driving component drives the sliding block to move towards the proximal end to return to its original position, and drives the rotation shaft to rotate inversely to return to its original position via the connecting rod.

As yet another improvement of the embodiment of the present invention, the driving component includes a first driving surface, a proximal end surface and a driving groove, which are all arranged on the cutter; the first driving surface is located at an upper inner edge of the proximal end of the driving groove; the proximal end surface is located at a lower outer edge of the driving groove.

As yet another improvement of the embodiment of the present invention, one end of the connecting rod is provided with a first pin hole, and the other end thereof with a second pin hole; the sliding block includes a main body having an upper end surface, a first pin shaft and an abutting portion having a distal end surface; the first pin shaft cooperates with the first pin hole of the connecting rod; the distal end surface of the abutting portion can cooperate with the proximal end surface of the cutter for restoring the sliding block.

As yet another improvement of the embodiment of the present invention, the rotation shaft includes a second pin shaft, a driving shaft, a first side wheel and a second side wheel; the second pin shaft cooperates with the second pin hole of the connecting rod; transverse outer ends of the first and second side wheels are pivotally connected to the staple cartridge bracket; transverse inner ends of the first and second side wheels are connected by the driving shaft; when the cutter push rod drives the cutter to move towards the distal end, the first driving surface of the cutter cooperates with the driving shaft of the rotation shaft to rotate the rotation shaft and to drive the sliding block via the connecting rod, such that the upper end surface of the main body of the sliding block moves to a position below the proximal end of the anvil; when the rotation shaft rotates for a certain angle, the first driving surface of the cutter is staggered with the driving shaft of the rotation shaft in the vertical direction, such that the cutter is detached from the rotation shaft, the rotation shaft stops rotating, and the cutter continues to move towards the distal end; when the cutter moves towards the proximal end to return to its original position, the proximal end surface of the cutter contacts the distal end surface of the sliding block, such that the sliding block is pushed to restore towards the proximal end, and the rotation shaft is driven to rotate inversely to return to its original position via the connecting rod.

As yet another improvement of the embodiment of the present invention, in the original status, the driving shaft is accommodated in the driving groove of the cutter.

As yet another improvement of the embodiment of the present invention, the second pin shaft of the rotation shaft is located at the second side wheel; an axial direction of the second pin shaft is parallel with a transverse direction of the staple cartridge bracket; the second side wheel includes an accommodating space for receiving the second pin shaft and the connecting rod; when the rotation shaft rotates, the accommodating space can provide sufficient pivoting space in which the connecting rod rotates around the second pin shaft.

As yet another improvement of the embodiment of the present invention, a side of the driving shaft away from the second pin shaft is provided with a containing groove for receiving a structure below the driving groove of the cutter.

As yet another improvement of the embodiment of the present invention, a driving shaft section of the rotation shaft is D-shaped, triangular, circular, rectangular, square or of an irregular shape.

As yet another improvement of the embodiment of the present invention, in a direction parallel with the bottom surface of the staple cartridge bracket and perpendicular with the axial direction of the sliding block, the first pin shaft of the sliding block and the abutting portion are arranged at the distal end of the main body in a staggered manner.

As yet another improvement of the embodiment of the present invention, at the proximal end of the main body of the sliding block is provided a guiding portion, which is a guiding block extending from the proximal end of the main body of the sliding block or a guiding groove arranged in the sliding block.

As yet another improvement of the embodiment of the present invention, the guiding portion and the abutting portion substantially overlap with the center axis of the rotation shaft and of the cutter; and the connecting rod is biased at a side of the center axis in a parallel manner.

As yet another improvement of the embodiment of the present invention, during a process in which the cutter drives the rotation shaft till it is detached therefrom, a maximum rotation angle of the rotation shaft is larger than 45 degrees but smaller than 150 degrees.

To realize one of the above objectives, an embodiment of the present invention provides a medical stapler including the staple cartridge assembly of any of the above technical solutions.

Compared with the prior art, the present invention may produce the following advantageous effects. By adopting the staple cartridge assembly and the medical stapler using the staple cartridge assembly of the present invention, the tension force applied to the cutter is effectively reduced in a use process, and the breakage of the cutter is avoided.

DETAILED DESCRIPTION

The present invention will now be described in detail with reference to specific embodiments as illustrated in the accompanying drawings. However, these embodiments are not intended to limit the present invention, and structures, methods, or functional changes made by one of ordinary skill in the art in accordance with these embodiments are included within the scope of the present invention.

The terms expressing the positions and directions used in the present invention use the instrument operator as the reference object. The end close to the operator is the proximal end, and the end far away from the operator is the distal end.

In the embodiments of the present invention, specific illustrations are made by taking an endoscopic surgical cutting stapler as an example. But it should be noted that other forms of staplers may be alternatively applied within the scope and spirit of the following embodiments.

Figure 1:
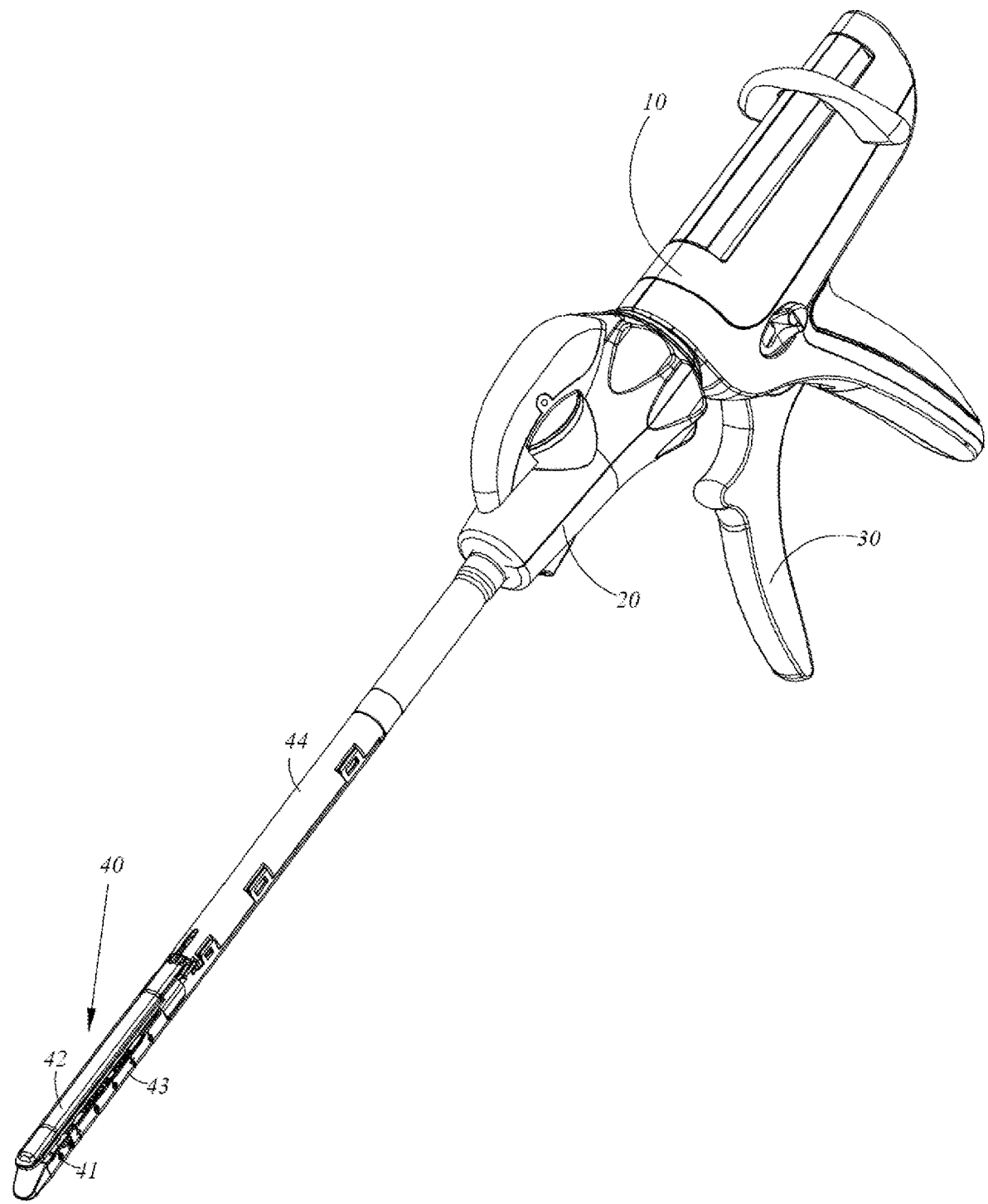
FIG. 1 a schematic structural view of a medical stapler according an embodiment of the present invention.
Figure 2:
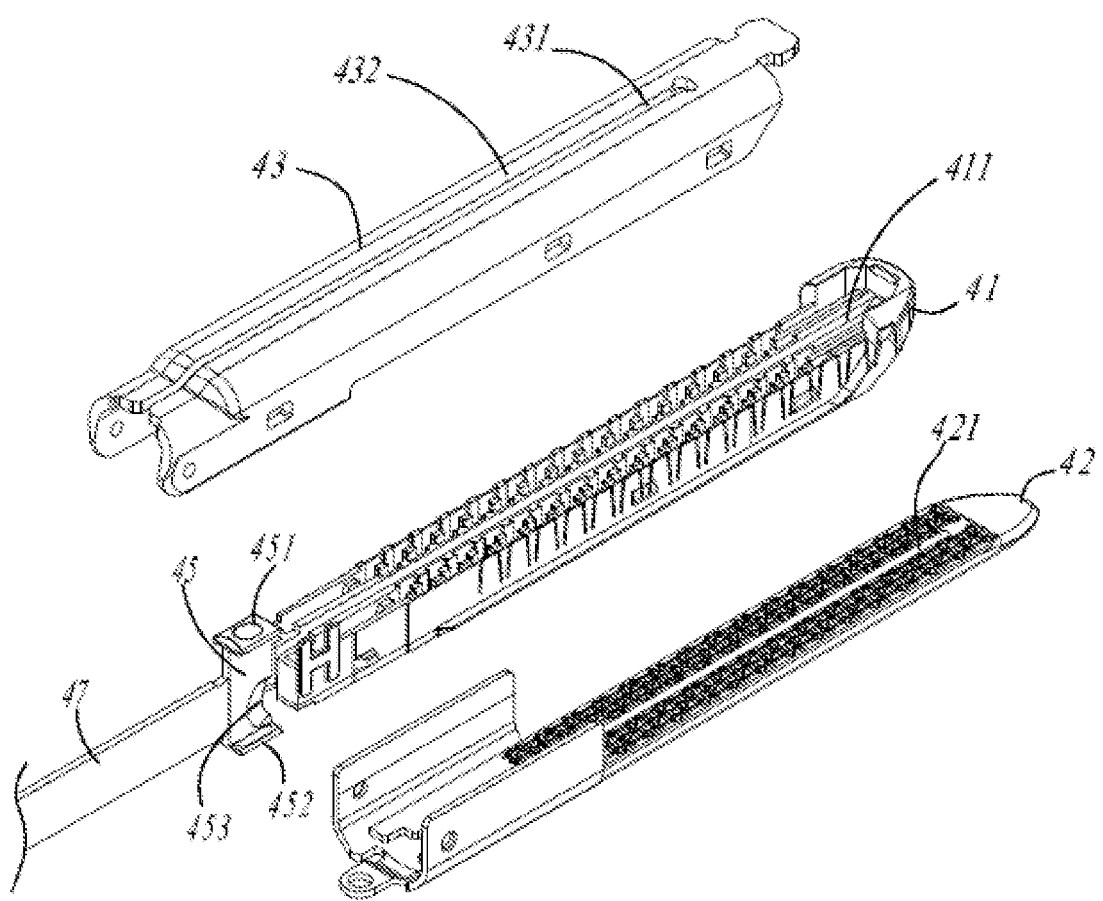
FIG. 2 is an exploded schematic view of a part of a staple cartridge assembly according an embodiment of the present invention.

As shown in FIGS. 1-2, a medical stapler is used for applying multiple staples onto physiological tissues of a human body and cutting the corresponding physiological tissues. The medical stapler includes an instrument main body 10, a rotation ring 20 matching with the instrument main body 10, and a firing handle 30 pivotally connected to the instrument main body 10.

The distal end of the instrument main body 10 is provided with a staple cartridge assembly 40.

The staple cartridge assembly 40 includes a staple cartridge 41, an anvil 42, a staple cartridge bracket 43, a connector 44 and a cutter 45.

The staple cartridge bracket 43 is detachably connected to the staple cartridge 41. Meanwhile, the staple cartridge bracket 43 is used for connecting the staple cartridge 41 with the connector 44.

In the present embodiment, the staple cartridge 41 and the anvil 42 can rotate relative to each other. When they rotate to open status, the operated target physiological tissues can be placed between the staple cartridge 41 and the anvil 42. Then, by rotating the staple cartridge 41 and the anvil 42 to closed status, the target physiological tissues between them are clamped to facilitate the followed cutting and suture operations.

In the present embodiment, when the medical stapler/staple cartridge assembly 40 is in an original status, the anvil tail at a proximal end of the anvil 42 is applied with an external force to keep the anvil 42 and the staple cartridge 41 in open status, and the cutter 45 is located at the proximal end of the staple cartridge assembly 40.

When the medical stapler/staple cartridge assembly 40 is in a closed status, the anvil 42 and the staple cartridge 41 are driven by the cutter 45 to be closed to each other. The target physiological tissues can be clamped between the anvil 42 and the staple cartridge 41. The cutter 45 moves a certain distance towards the distal end of the medical stapler/staple cartridge assembly 40 relative to the original status. But generally, the cutter 45 is still located at the proximal end of the staple cartridge assembly 40.

When the medical stapler/staple cartridge assembly 40 is in a firing status, the anvil 42 and the staple cartridge 41 are kept to be closed to each other, and the cutter 45 moves from the proximal end of the staple cartridge assembly 40 to the distal end thereof, cuts the clamped physiological tissues, and stops moving at the distal end of the staple cartridge assembly 40 when being limited.

When the medical stapler/staple cartridge assembly 40 is in a state of finishing a firing process, the cutter 45 moves back to a position where it is in the original status, the anvil 42 and the staple cartridge 41 are in open status, and the cutter 45 is located at the proximal end of the staple cartridge assembly 40.

In the present embodiment, as shown in FIG. 2, the cutter 45 includes a first end 451, a second end 452 and a cutting part which is arranged between the first end 451 and the second end 452. The cutting part is provided with a blade 453.

The staple cartridge assembly 40 also includes a rotation shaft 50 and an auxiliary closing member which is connected with the rotation shaft 50. The rotation shaft 50 is arranged at the proximal end of the staple cartridge assembly 40 relative to the blade 453.

The staple cartridge assembly 40 is also provided with a driving component 51 capable of driving the rotation shaft 50 to rotate. The driving component 51 drives the rotation shaft 50 to drive the auxiliary closing member to move during the process in which the staple cartridge assembly 40 is converted from an original status to a closed status. When at least the staple cartridge assembly 40 is in the closed status, one end surface of the auxiliary closing member abuts against the anvil 42 to apply a force to the anvil 42 for driving the anvil 42 to be closed towards the staple cartridge 41.

In one embodiment of the present invention, as shown in FIG. 2, the staple cartridge bracket 43 includes a first abutting surface 432 which is far away from the anvil 42 and cooperates with the first end 451 of the cutter 45; and a second abutting surface which backs the anvil surface and cooperates with the second end 452 of the cutter 45.

The staple cartridge 41, the anvil 42 and the staple cartridge bracket 43 are provided with cutter receiving grooves 411, 421, 431 respectively to cooperate with the cutter 45. The cutter receiving grooves 411, 421, 431 extend from the proximal ends of the staple cartridge 41, the anvil 42 and the staple cartridge bracket 43 to the distal ends thereof respectively. When the anvil 42 and the staple cartridge 41 are closed to each other, the cutter receiving grooves 411, 421, 431 cooperate with one another to form a passage along which the cutter 45 can move from the proximal end of the staple cartridge assembly 40 to the distal end thereof or from the distal end thereof to the proximal end thereof.

The staple cartridge assembly 40 further includes a cutter push rod 47 connected to the proximal end of the cutter 45. The cutter push rod 47 can drive the cutter 45 to move from the proximal ends of the cutter receiving grooves 411, 421, 431 to the distal ends thereof or from the distal ends thereof to the proximal ends thereof.

The structure of the staple cartridge assembly 40 will now be described in detail with reference to the accompanying drawings of the first embodiment and the second embodiment, respectively.

First, the first embodiment will be described with reference to FIGS. 3 to 21.

Figure 3:
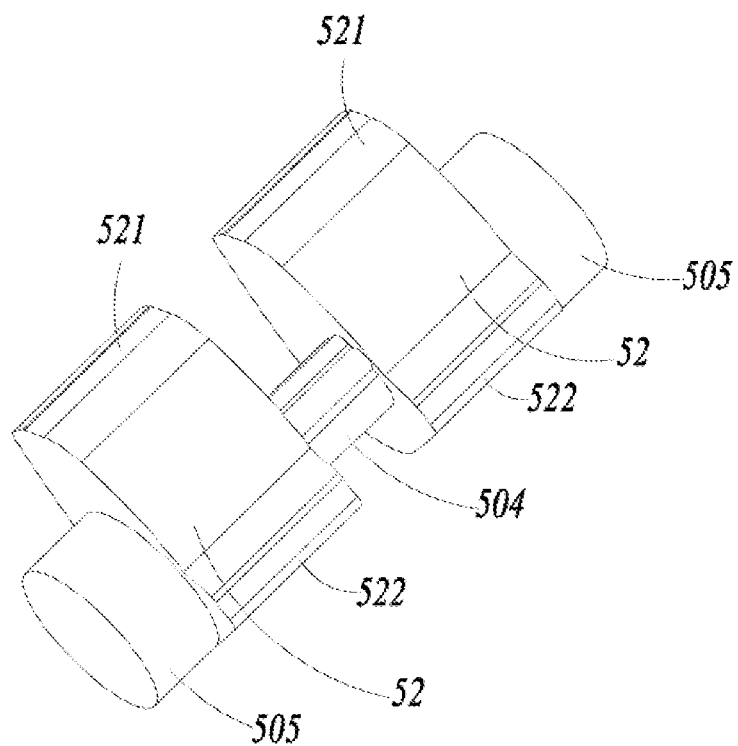
FIG. 3 is a stereogram of a cam and a rotation shaft according to the first embodiment of the present invention.
Figure 4:
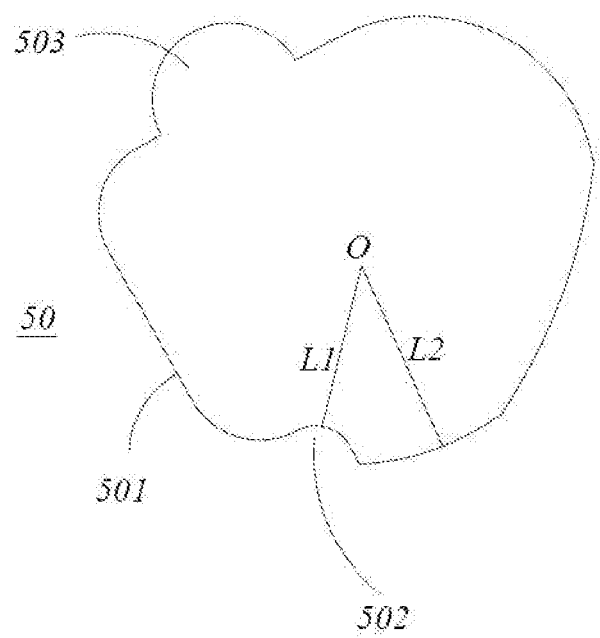
FIG. 4 is a schematic structural view of the rotation shaft according to the first embodiment of the present invention.

Referring to FIG. 3 and FIG. 4, in the first embodiment, the rotation shaft 50 includes two side wheels 505 and a driving shaft 504 located between the two side wheels 505. The driving shaft 504 of the rotation shaft 50 includes at least one concave portion 502 and a contact portion 501, wherein the lowest point of the concave portion 502 is closer to an axis O of the rotation shaft 50 than the lowest point of the contact portion 501; that is, a distance L1 from the lowest point of the concave portion 502 to the axis O is less than a distance L2 from the lowest point of the contact portion 501 to the axis O. The rotation shaft 50 may further include at least one convex portion 503 which may be convexly arranged in a position of the contact portion 501 where the concave portion 502 is not located.

Figure 5:
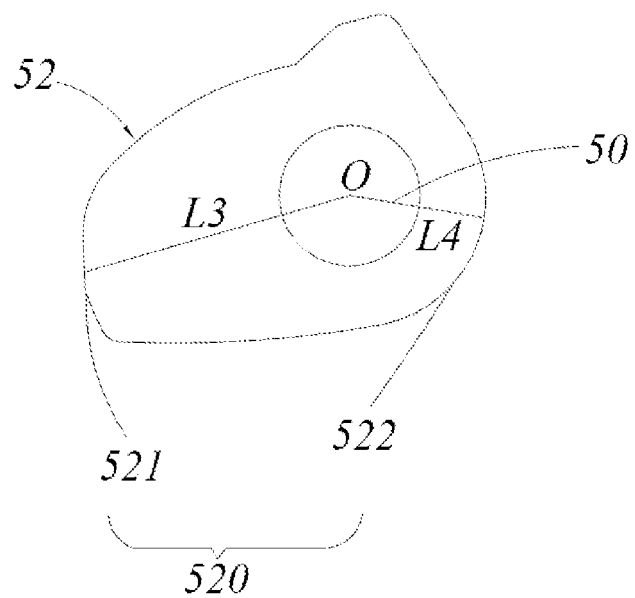
FIG. 5 is a schematic structural view of the cam according to the first embodiment of the present invention.

Referring to FIG. 3 and FIG. 5, in the first embodiment, the auxiliary closing member includes a cam 52 fixedly connected to the rotation shaft 50. The cam 52 is rotatable in synchronization with the driving shaft 504 around the axis O of the rotation shaft 50.

In the present embodiment, the auxiliary closing member includes two cams 52 which are located at both sides of the driving shaft 504, respectively, i.e., are located at both sides of the cutting part of the cutter 45, respectively. The cam 52 is provided with a cam surface 520. The cam surface 520 includes an abutting portion 521 and a smooth portion 522, wherein the highest point of the abutting portion 521 is farther to the axis O of the rotation shaft 50 than the highest point of the smooth portion 522; that is, a distance L3 from the highest point of the abutting portion 521 to the axis O is greater than a distance L4 from the highest point of the smooth portion 522 to the axis O.

In the first embodiment, the rotation shaft 50 and the cam 52 are integrally arranged. Of course, during specific implementation, the rotation shaft 50 may also be arranged separately from the cam 53.

Figure 6:
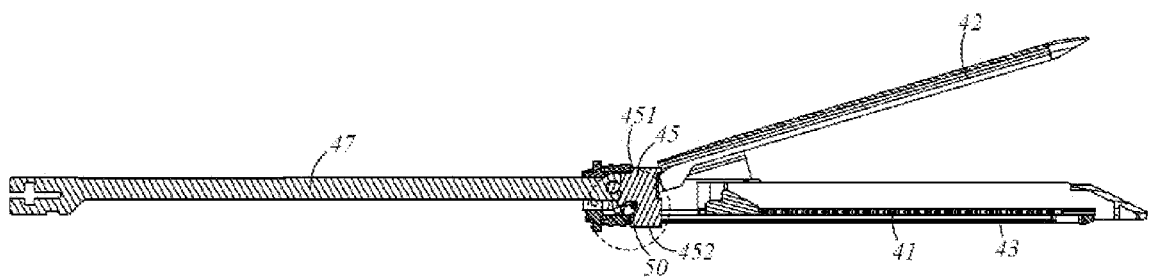
FIG. 6 is a schematic sectional view of the rotation shaft when the staple cartridge assembly is in an original status according the first embodiment of the present invention.
Figure 7:
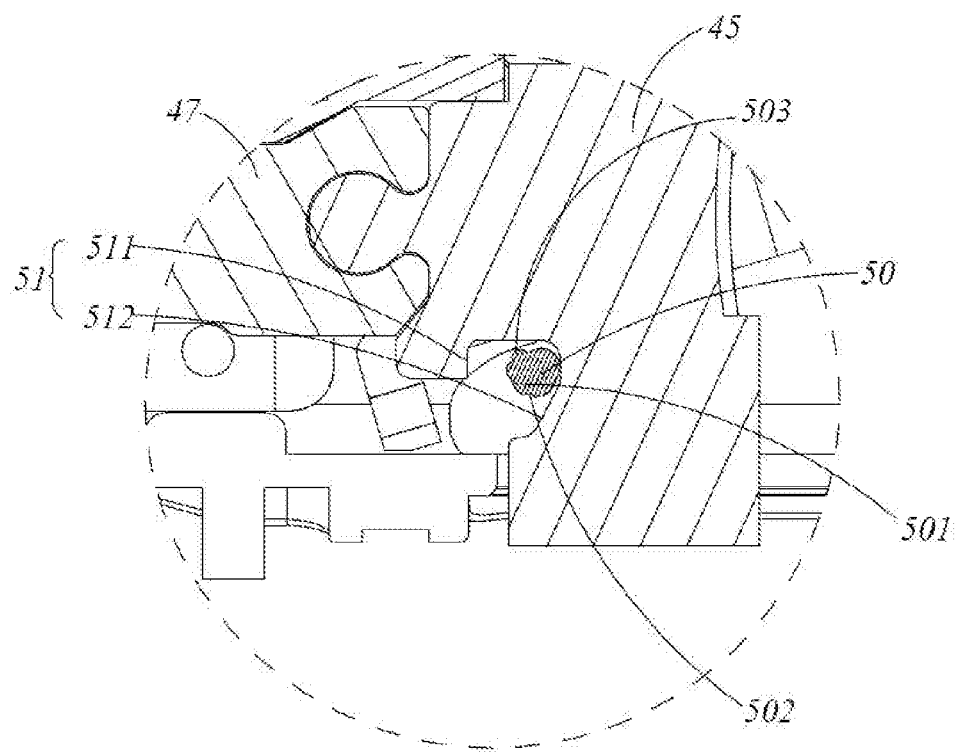
FIG. 7 is a locally enlarged schematic structural view of FIG. 6.

Referring to FIG. 6 and FIG. 7, in the first embodiment, the driving component 51 is formed in a proximal end region of the cutting part of the cutter 45, is arranged as a groove in the cutter 45 and is integrally formed together with the cutter 45. Of course, the driving component 51 may also be detached from the cutter 45.

The driving component 51 includes a first driving surface 511 and a second driving surface 512, wherein the first driving surface 511 is located at the proximal end of the second driving surface 512. In the present embodiment, the first driving surface 511 may be arranged as a hooked surface at one end of the groove, and the second driving surface 512 is arranged as a surface opposite to the first driving surface 511.

Figure 8:
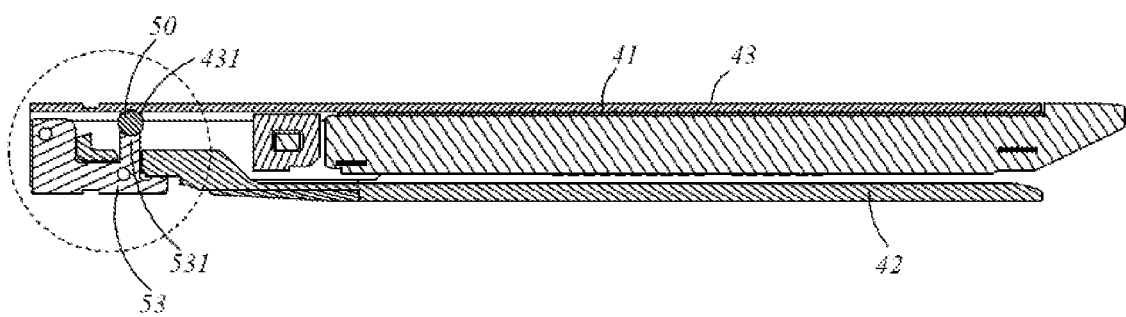
FIG. 8 is a schematic sectional view when the rotation shaft is fixed according to the first embodiment of the present invention.
Figure 9:
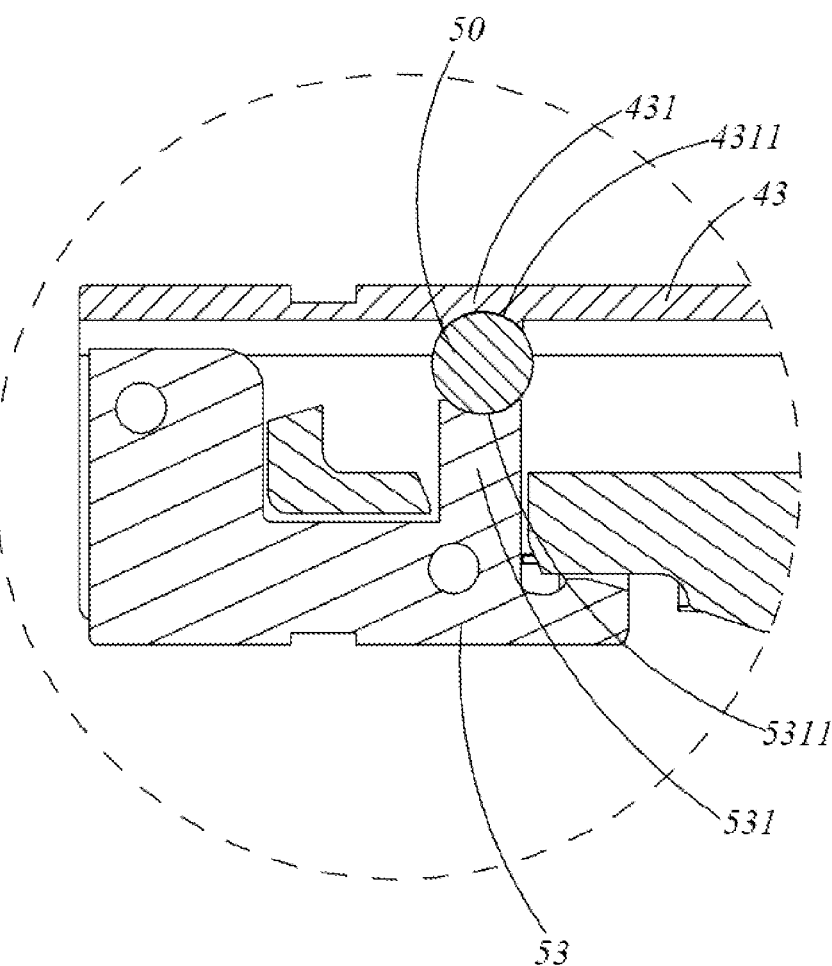
FIG. 9 is a locally enlarged schematic structural view of FIG. 8.
Figure 10:
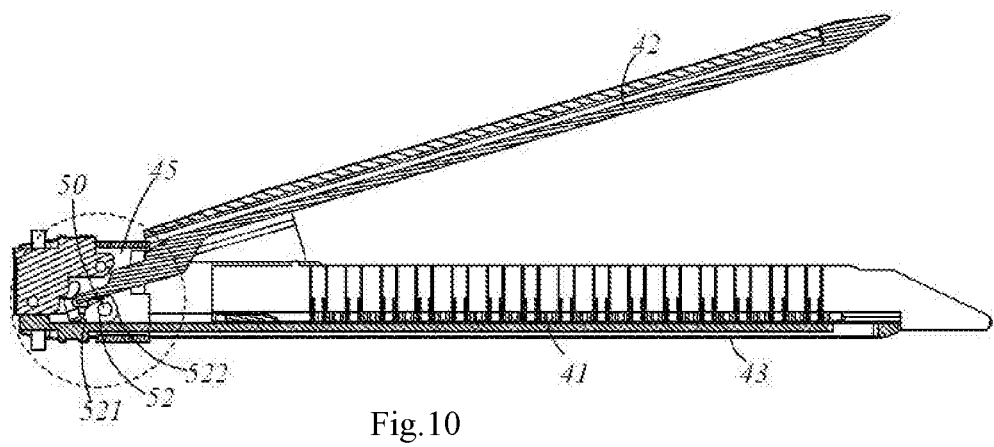
FIG. 10 is a schematic sectional view of the cam when the staple cartridge assembly is in an original status according the first embodiment of the present invention.
Figure 11:
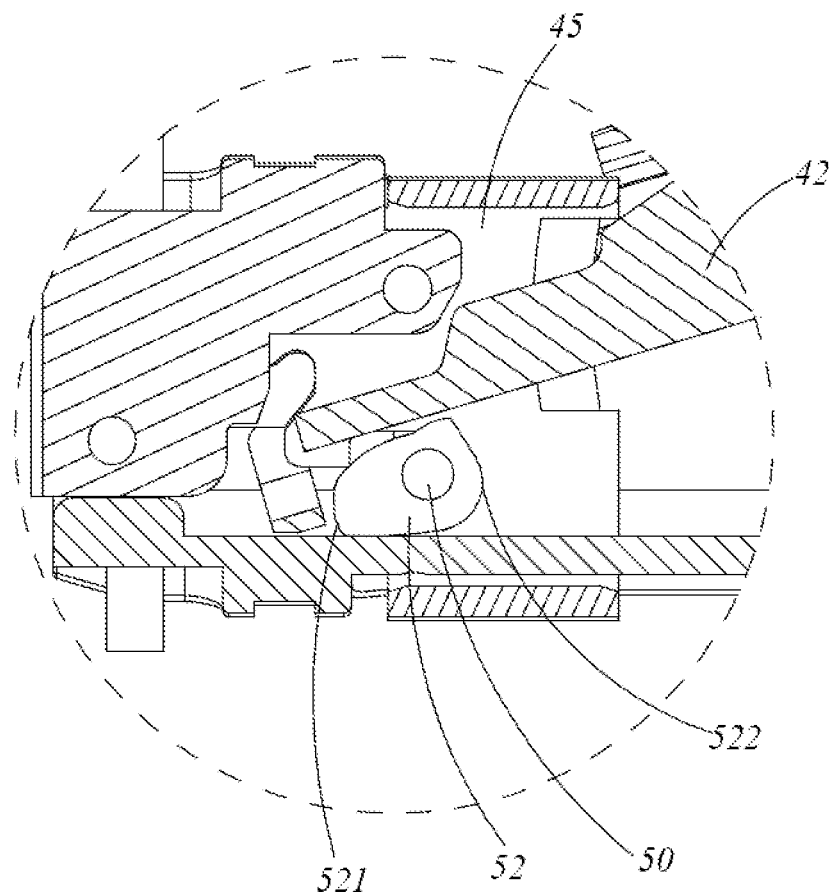
FIG. 11 is a locally enlarged schematic structural view of FIG. 10.
Figure 12:
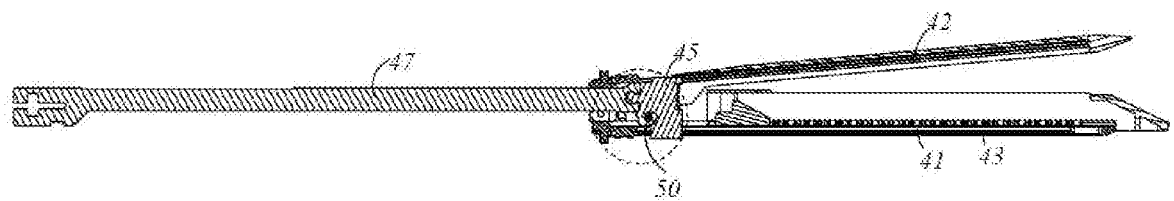
FIG. 12 is a schematic sectional view of the rotation shaft during a process in which the staple cartridge assembly is converted from an original status to a closed status according the first embodiment of the present invention.
Figure 13:
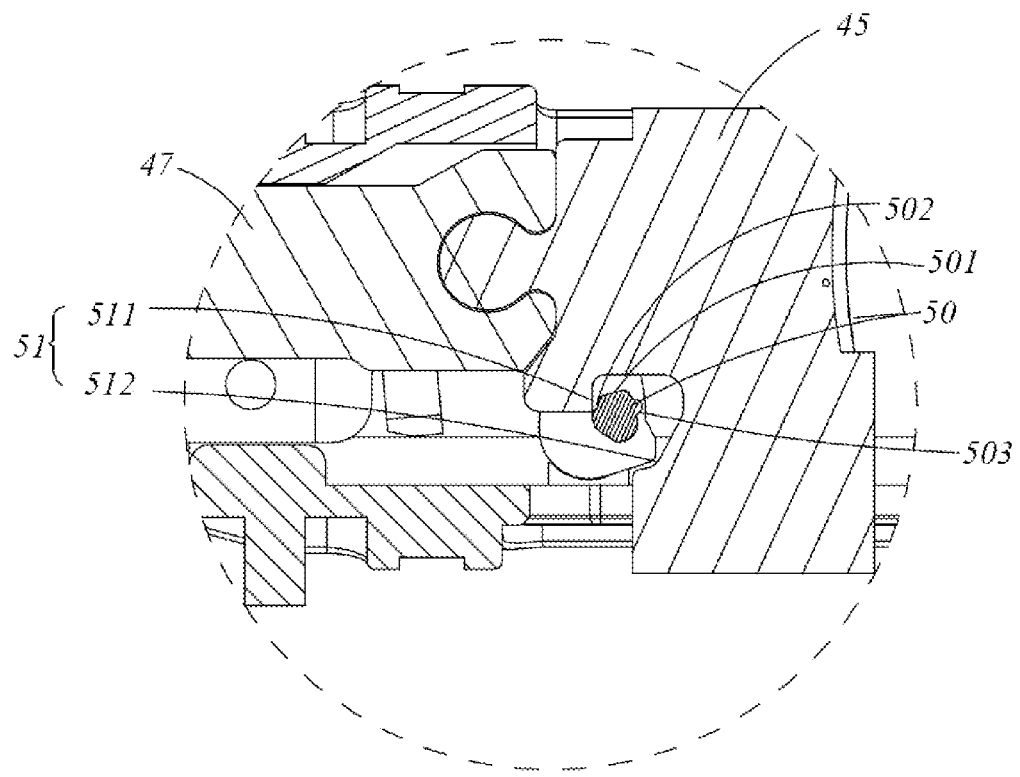
FIG. 13 is a locally enlarged schematic structural view of FIG. 12.
Figure 14:
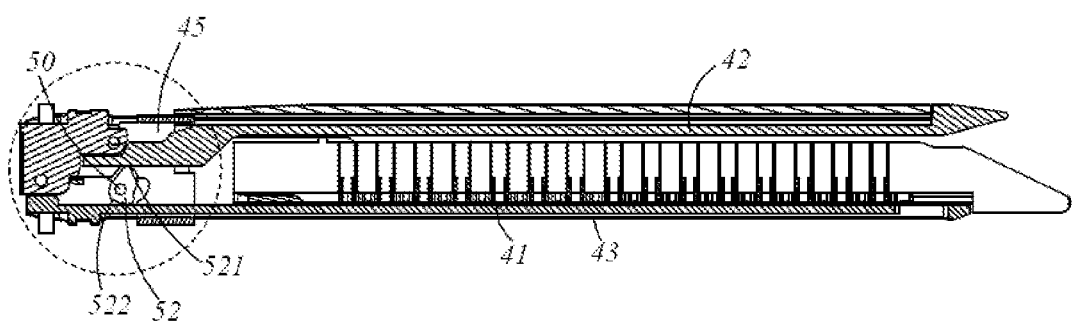
FIG. 14 is a schematic sectional view of the cam when the staple cartridge assembly is in a closed status according the first embodiment of the present invention.
Figure 15:
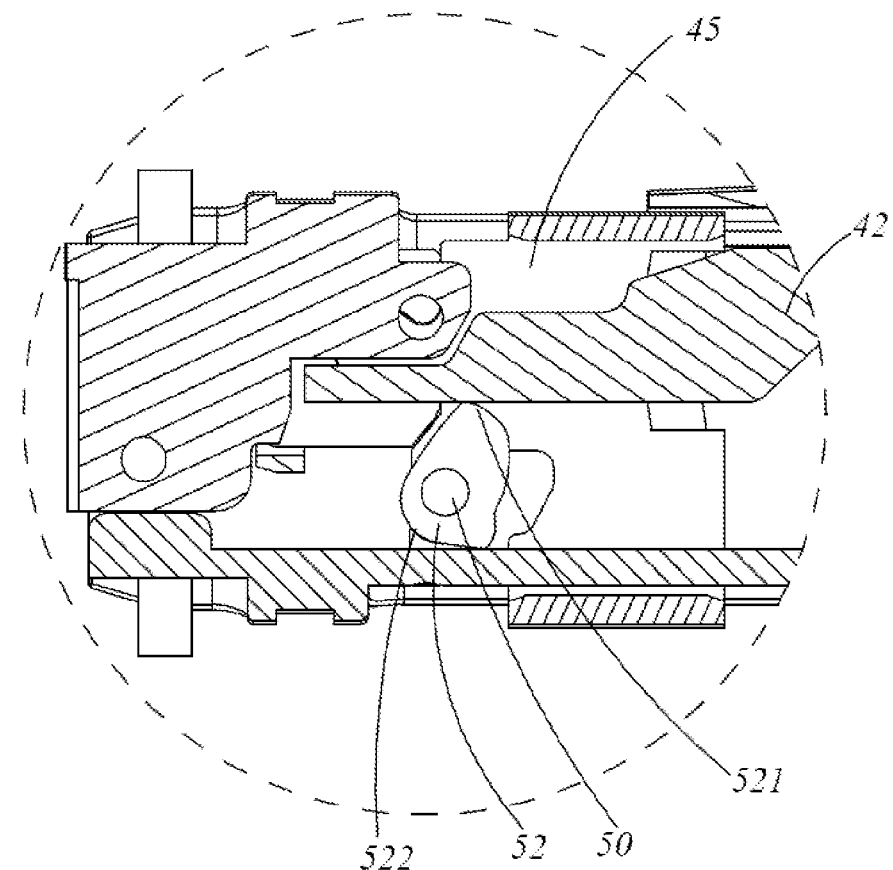
FIG. 15 is a locally enlarged schematic structural view of FIG. 14.

As shown in FIG. 8 and FIG. 9, the staple cartridge assembly 40 further includes an adapter 53 which is used for connecting the connector 44 and the staple cartridge bracket 43. The two side wheels 505 of the rotation shaft 50 may be arranged as cylinders. The adapter 53 cooperates with the staple cartridge bracket 43 to form an accommodating space in which the side wheels 505 of the rotation shaft 50 rotate smoothly and in which at least part of the side wheels 505 of the rotation shaft 50 is arranged. As such, the support to the rotation shaft 50 is realized, and the rotation shaft 50 is limited to be rotatable only within the accommodating space.

The adapter 53 is provided with a fixing portion 531 cooperating with the staple cartridge bracket 43. An end surface of the fixing portion 531 close to the staple cartridge bracket 43 is arranged as a first arced surface 5311. A protrusion 431 corresponding to the fixing portion 531 convexly extends on the staple cartridge bracket 43. An end surface of the protrusion 431 close to the fixing portion 531 is arranged as a second arced surface 4311. The first arced surface 5311 and the second arced surface 4311 together define the accommodating space.

In the present embodiment, the adapter 53 includes the two fixing portions 531 located at both sides of the cutting part of the cutter 45 respectively. The staple cartridge bracket 43 includes two corresponding protrusions 431. The circumferential outer surface of the rotation shaft 50 is adaptive with the first arced surface 5311 and the second arched surface 4311 and limited between the two fixing portions 531 and the two protrusions 431.

The specific working process of the staple cartridge assembly 40 in the present embodiment is as follows.

As shown in FIGS. 6-11, the staple cartridge assembly 40 is in an original status; the first driving surface 511 is far away from the driving shaft 504; the smooth portion 522 of the cam 52 is adjacent to the anvil 42; the smooth portion 522 is spaced from the anvil 42 for a certain distance; and the cam 52 is detached from the anvil 42 to each other.

As shown in FIGS. 12-15, the cutter 45 moves towards the distal end of the staple cartridge assembly 40 during the process in which the staple cartridge assembly 40 is converted from an original status to a closed status, such that the staple anvil 42 rotates towards the staple cartridge 41 to realize closing. The first driving surface 511 gradually approaches and contacts the contact portion 501 of the driving shaft 504 to drive the rotation shaft 50 to rotate towards a first direction. The cam 52 rotates in synchronization with the rotation shaft 50, and the abutting portion 521 of the cam 52 gradually approaches and abuts against the anvil 42. When at least the staple cartridge assembly 40 is in the closed status, two cams 52 abut against anvil 42 at both sides of the cutter receiving groove 421 simultaneously to apply a force to the anvil 42 for driving the anvil 42 to be closed towards the staple cartridge 41. Meanwhile, the concave portion 502 of the driving shaft 504 rotates to a portion of the first driving surface 511 close to the staple cartridge bracket 43. As such, the tension force applied to the cutter 45 is correspondingly reduced since the cam 52 assists the anvil 42 and the staple cartridge 41 to be closed.

Figure 16:
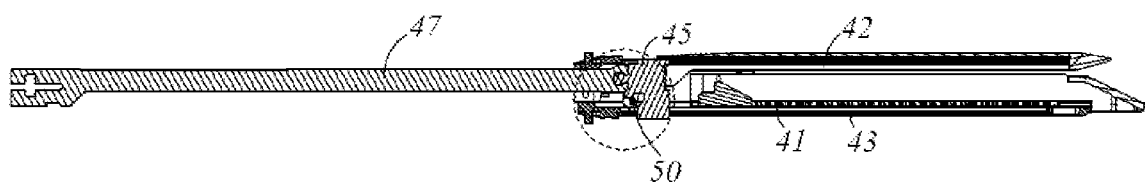
FIG. 16 is a schematic sectional view of the rotation shaft during a process in which the staple cartridge assembly is fired according the first embodiment of the present invention.
Figure 17:
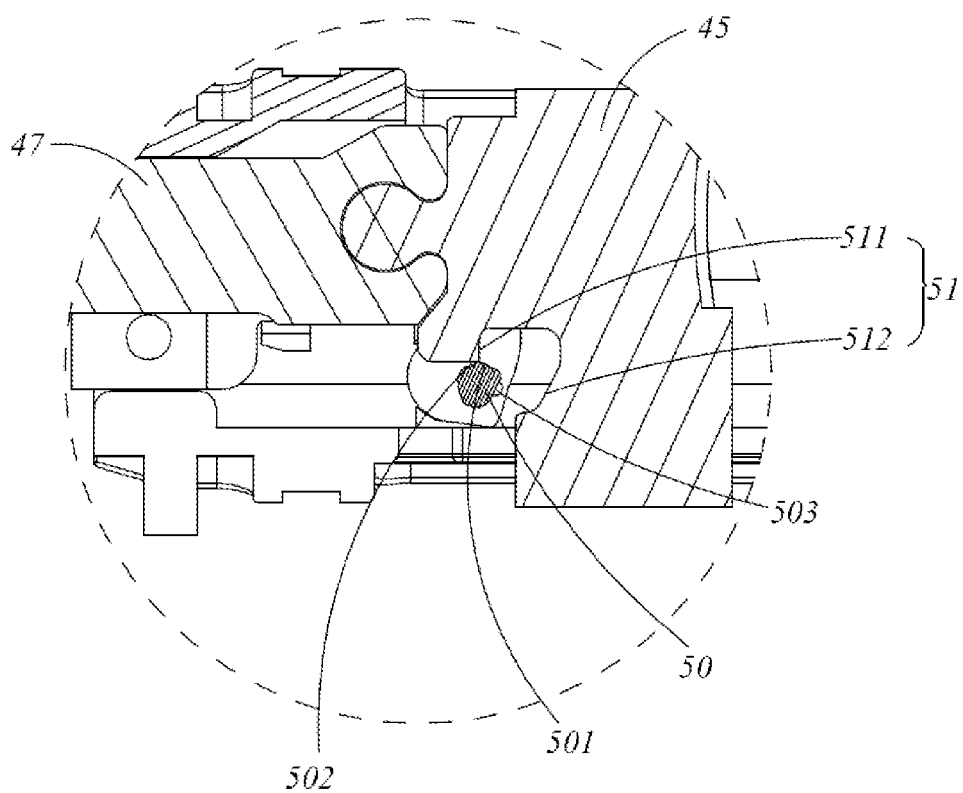
FIG. 17 is a locally enlarged schematic structural view of FIG. 16.
Figure 18:
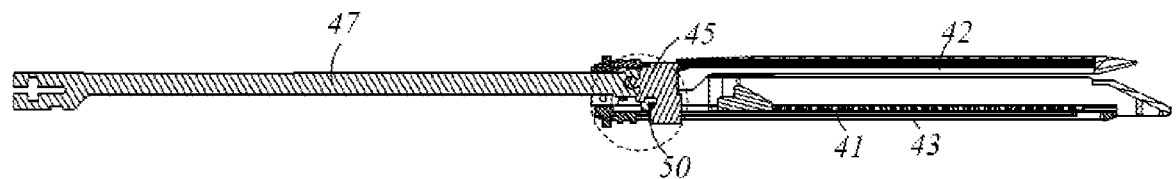
FIG. 18 is a schematic sectional view of the rotation shaft during a process in which the staple cartridge assembly returns to its original status after being fired according the first embodiment of the present invention.
Figure 19:
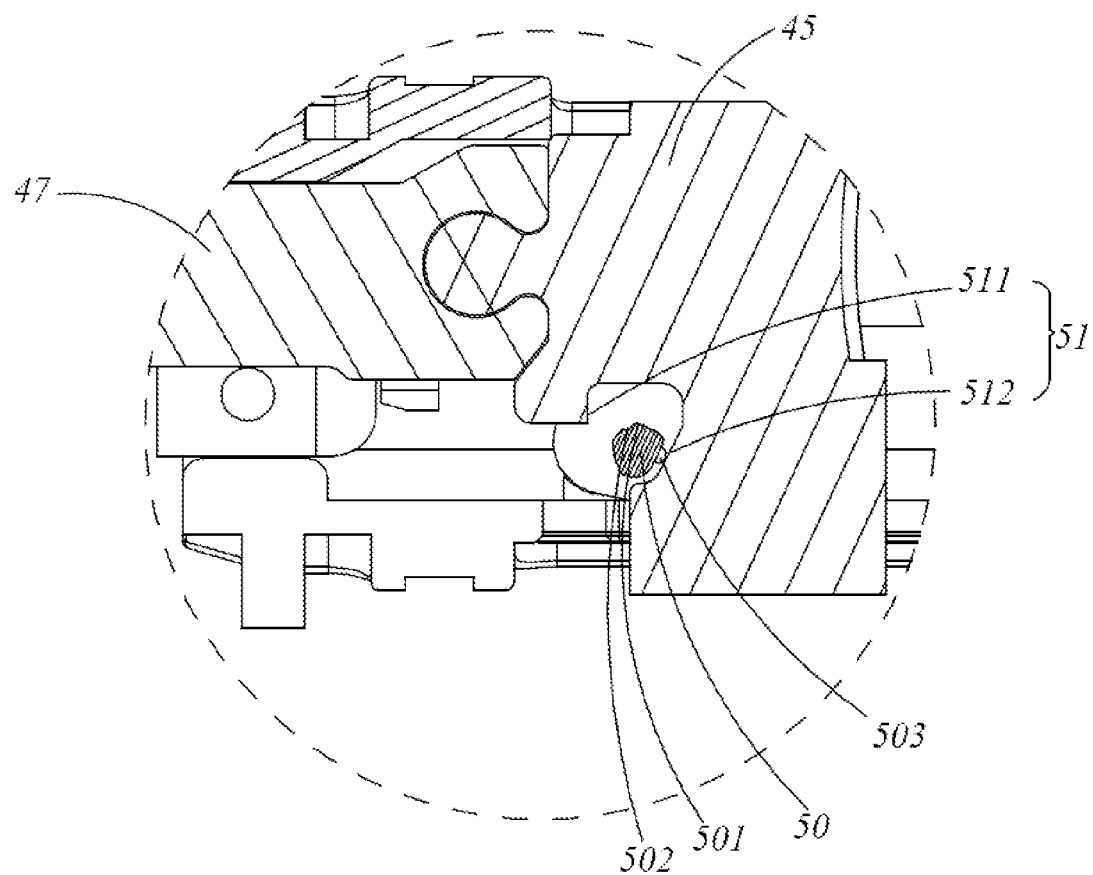
FIG. 19 is a locally enlarged schematic structural view of FIG. 18.
Figure 20:
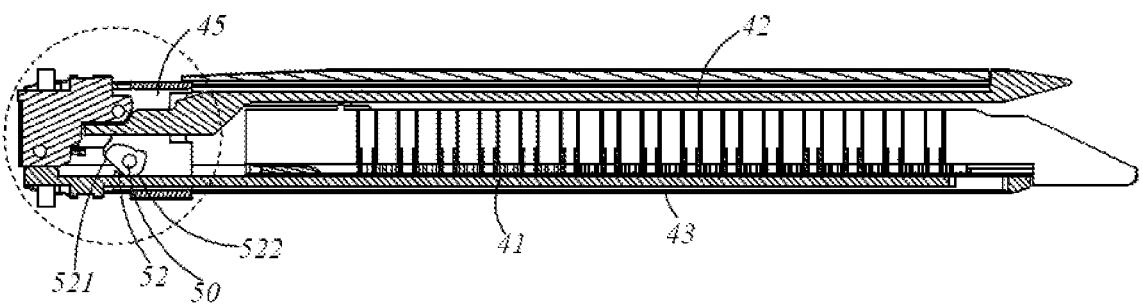
FIG. 20 is a schematic sectional view of the cam after the staple cartridge assembly returns to its original status according the first embodiment of the present invention.
Figure 21:
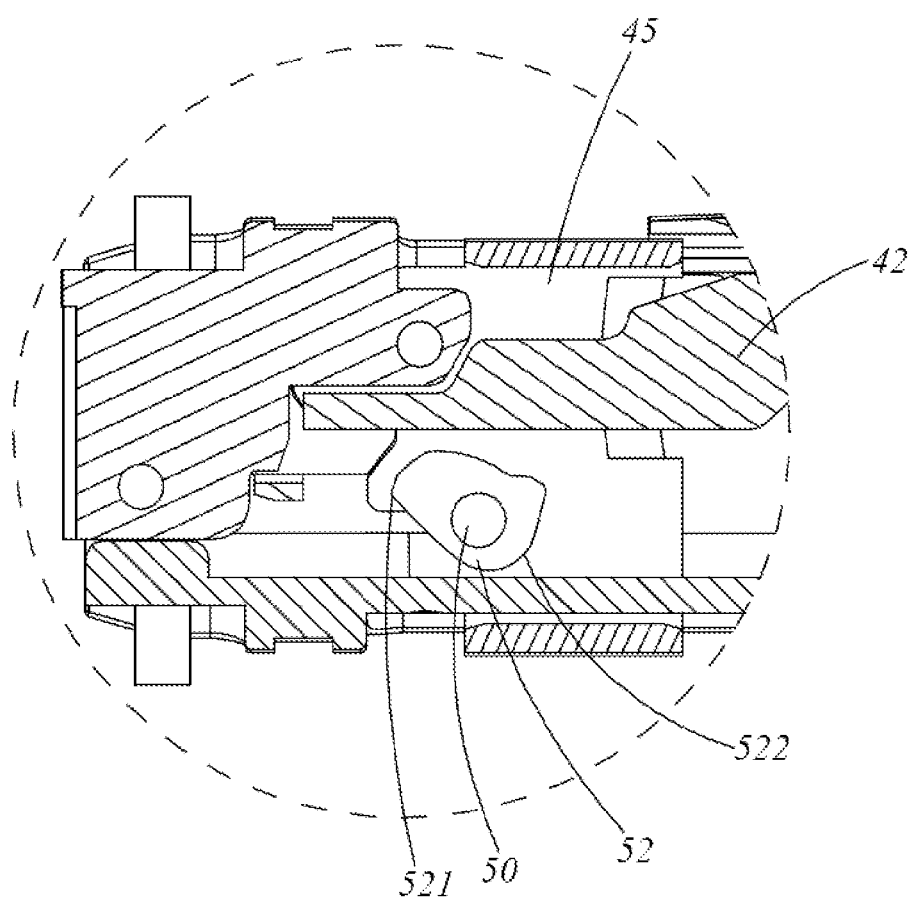
FIG. 21 is a locally enlarged schematic structural view of FIG. 20.

As shown in FIGS. 16-17, since the concave portion 502 of the driving shaft 504 rotates to the portion of the first driving surface 511 close to the staple cartridge bracket 43 after the anvil 42 and the staple cartridge 41 are closed, even if the cutter 45 continues to move towards the distal end, the driving shaft 504 cannot continue to cooperate with the first driving surface 511 to rotate. Therefore, when the staple cartridge assembly 40 begins to be fired, the cutter 45 continues to move towards the distal end of the staple cartridge assembly 40, and the driving component 51 is detached from the rotation shaft 50. The cutter 45 may be detached from the rotation shaft 50 and continues to move towards the distal end of the staple cartridge assembly 40. The rotation shaft 50 maintains to be always stationary during the process in which the rotation shaft 50 is detached from the driving component 51. The abutting portion 521 of the cam 52 always abuts against the anvil 42 and always assists the anvil 42 and the staple cartridge 41 to be closed, thereby ensuring that the force is always applied to the proximal end portion of the anvil 42 in a firing process of the staple cartridge assembly 40.

As shown in FIGS. 18-21, during a process of returning to the original status of the staple cartridge assembly 40 after being fired, the cutter 45 moves from the distal end of the staple cartridge assembly 40 towards the proximal end thereof, and the second driving surface 512 gradually approaches and contacts the convex portion 503 to drive the rotation shaft 50 to rotate towards a second direction. The abutting portion 521 of the cam 52 is detached from the anvil 42, such that the cam 52 and the anvil 42 are detached from each other finally.

After the staple cartridge assembly 40 has finished its firing process, each of the cam 52, the rotation shaft 50 and the cutter 45 returns to its original status. The second direction is opposite to the first direction, and in view of an angle as shown in drawings, the first direction is a clockwise direction, and the second direction is an anticlockwise direction.

A cam 52 in one embodiment of the present invention rotates under the action of the driving component 51 and the rotation shaft 50, and the cam 52 at least abuts against the anvil 42 in a closed status and assists the anvil 42 to be closed towards the staple cartridge 41, thereby reducing the tension force applied to the cutter 45 and avoiding the breakage of the cutter 45. In the closed status and during the firing process of the staple cartridge assembly 40, the cam surface 520 of the cam 52 always abuts against the anvil 42 to further reduce the tension force applied to the cutter 45 in the firing process, avoid poor forming of staples due to the larger tension force applied to the cutter 45 and reduce the operation risk The second embodiment will be described as below with reference to FIGS. 22 to 32.

Figure 22:
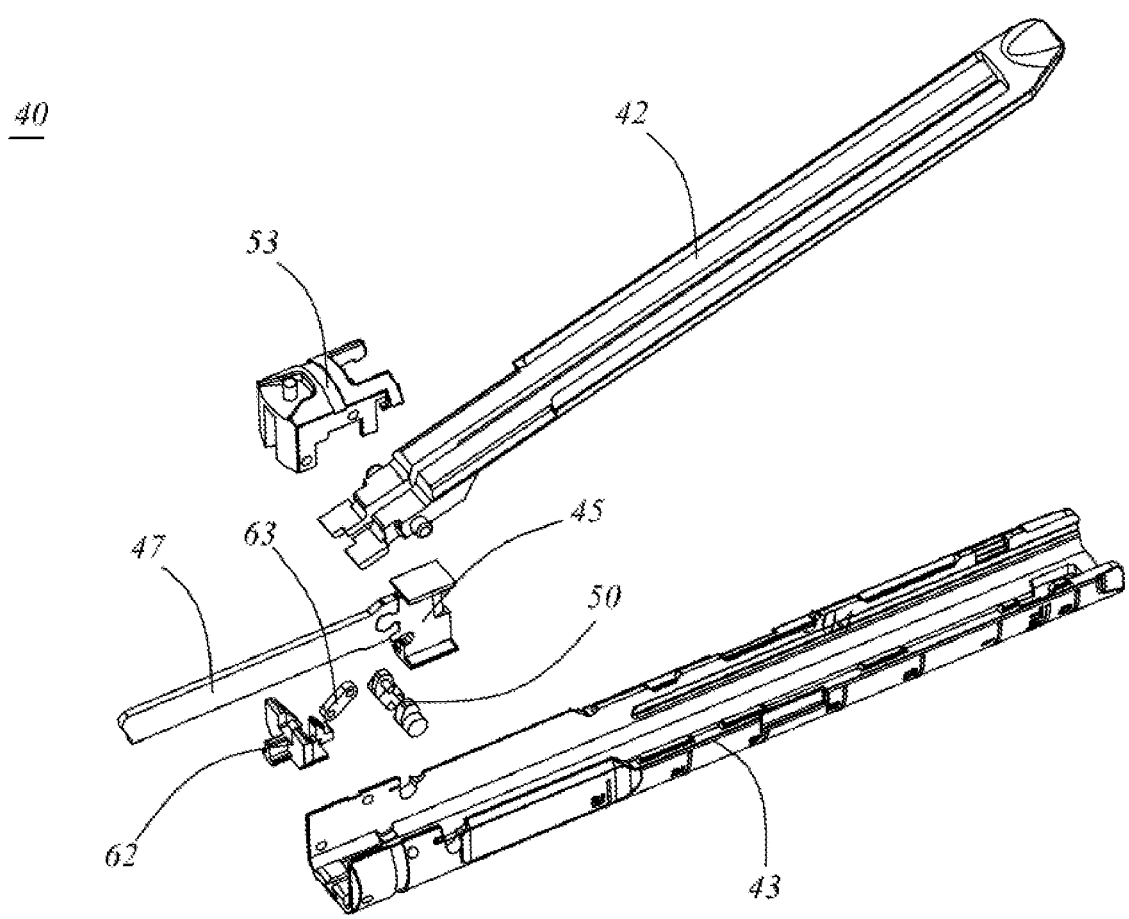
FIG. 22 is an exploded schematic view of a part of the staple cartridge assembly according the second embodiment of the present invention.

First, referring to FIG. 22, similar to the first embodiment, the second embodiment of the present invention provides a staple cartridge assembly 40 of a stapler, including a staple cartridge bracket 43, an anvil 42, a cutter 45, a cutter push rod 47, a rotation shaft 50 and the auxiliary closing member. The staple cartridge bracket 43 is used for accommodating a detachable staple cartridge (not shown). The anvil 42 is provided with a staple forming groove which corresponds to a staple placing hole in the staple cartridge and a staple in the staple placing hole and which is used for suturing target physiological tissues. The cutter 45 is used for cutting the target physiological tissues and includes, but is limited to, an I-shaped cutter having an I-shaped cross section. The cutter push rod 47 is used for driving the cutter 45 to move to clamp the target physiological tissues, and meanwhile can be implemented to cut and suture the target physiological tissues.

Figure 23:
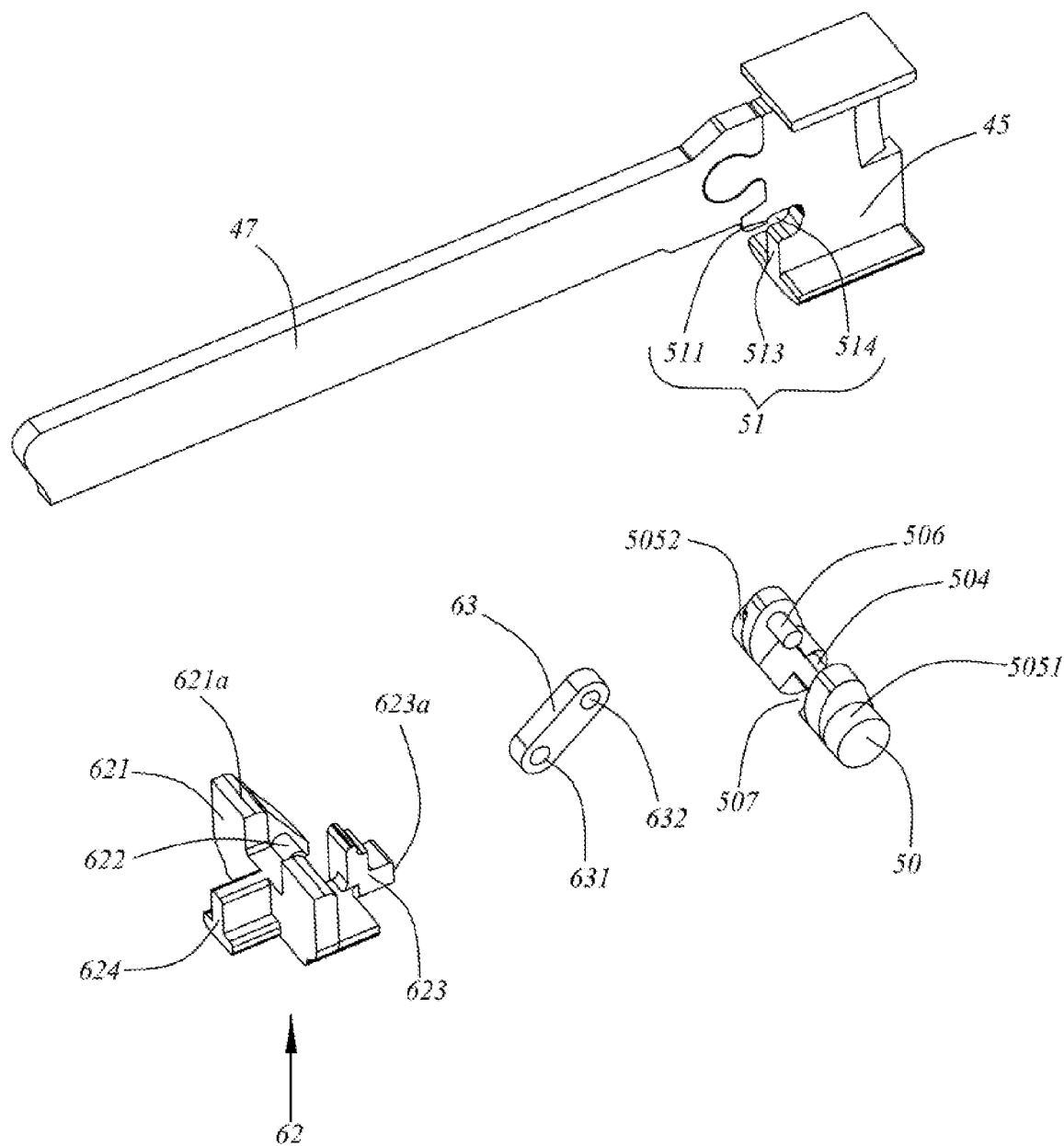
FIG. 23 is a schematic structural view of a part of the staple cartridge assembly according the second embodiment of the present invention.

Referring to FIG. 23, the second embodiment differs from the first embodiment in that, in the second embodiment, the rotation shaft 50 is movably arranged separate from the auxiliary closing member.

Specifically, the rotation shaft 50 includes a first side wheel 5051 and a second side wheel 5052, a driving shaft 504 located between the first side wheel 5051 and the second side wheel 5052, and a second pin shaft 506. The rotation shaft 50 is pivotally connected to the staple cartridge bracket 43 via the first side wheel 5051 and/or the second side wheel 5052 and is rotatable relative to the staple cartridge bracket 43 for a certain angle, for example, rotatable for 30 to 120 degrees in the clockwise direction.

The auxiliary closing member is arranged in the staple cartridge bracket 43 and includes a sliding block 62 and a connecting rod 63. The two ends of the connecting rod 63 are pivotally connected to the sliding block 62 and the rotation shaft 50 respectively.

When the cutter push rod 47 drives the cutter 45 to move towards the distal end, the driving component 51 can drive the rotation shaft 50 to rotate for a certain angle and drive the sliding block 62 to move via the connecting rod 63, such that the sliding block 62 moves to a position below a proximal end of the anvil 42 to support the proximal end of the anvil 42 and to assist the anvil 42 to be closed. As the cutter push rod 47 drives the cutter 45 to continue to move towards the distal end, the driving component 51 is detached from the rotation shaft 50, the rotation shaft 50 stops rotating, and the cutter 45 still moves towards the distal end till the stapler has finished the process of cutting and suturing the target physiological tissues. When the cutter 45 is pulled to restore from the distal end to the proximal end after the stapler has finished the process of cutting and suturing the target physiological tissues, the driving component 51 can drive the distal end of the sliding block 62, such that the sliding block 62 moves towards the proximal end to return to its original position and drives the rotation shaft 50 to rotate inversely to return to its original position via the connecting rod 63.

Figure 24:
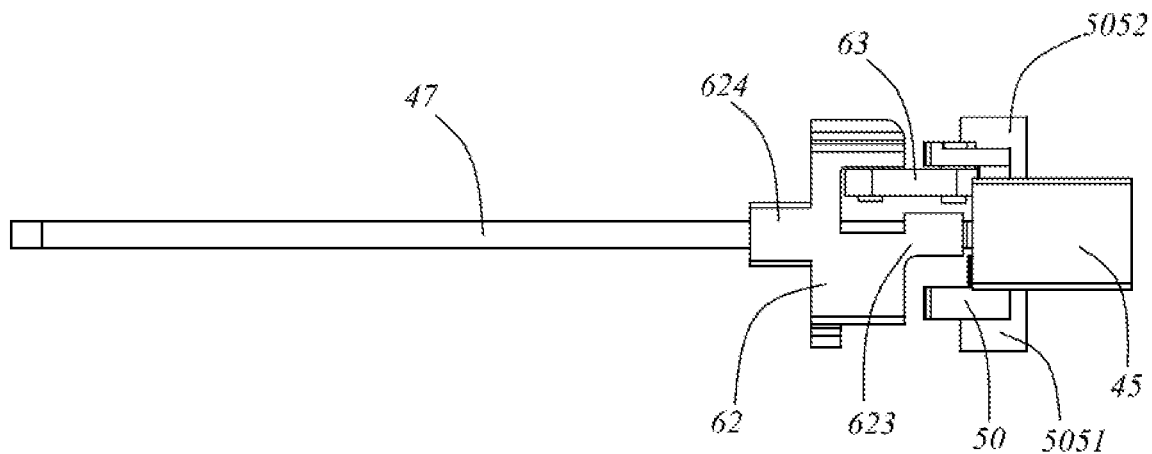
FIG. 24 is a plan view after the structure in FIG. 23 is assembled.
Figure 25:
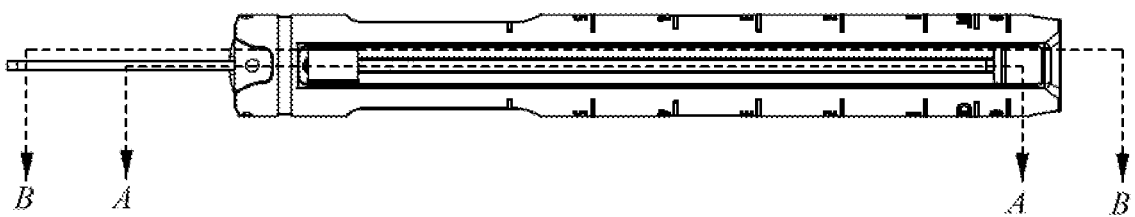
FIG. 25 is a plan view after the staple cartridge assembly is assembled according the second embodiment of the present invention.
Figure 26A:
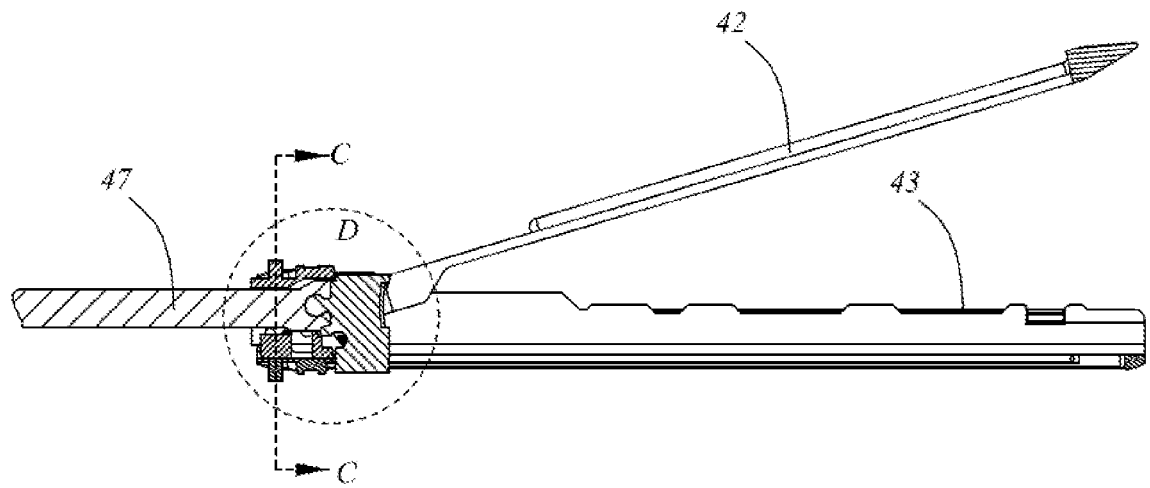
FIG. 26A is a sectional view along line A-A in FIG. 25.
Figure 26B:
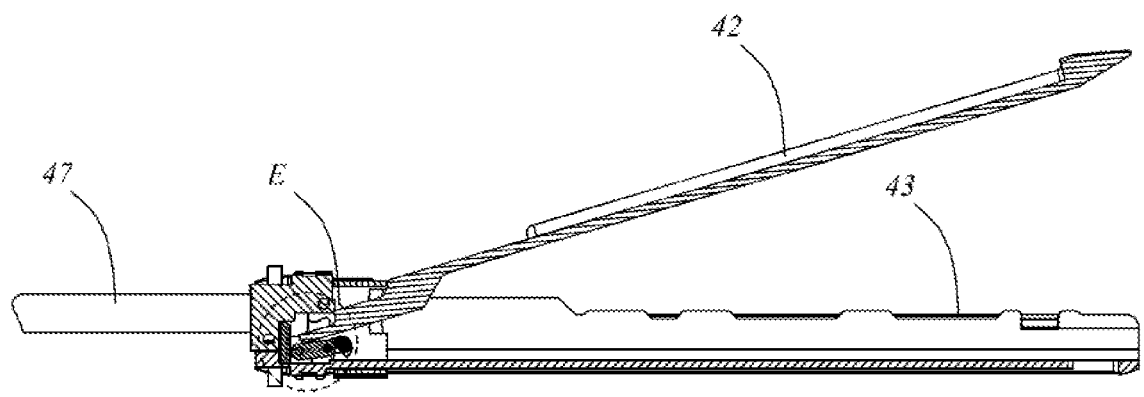
FIG. 26B is a sectional view along line B-B in FIG. 25.

As shown in FIG. 23 and FIG. 24, in the staple cartridge assembly 40 of the stapler, the driving component 51 includes a first driving surface 511 arranged at the proximal end of the cutter 45, a proximal end surface 513 and a driving groove 514. The driving component 51 and the cutter 45 are integrally formed, and therefore, a driving effect of the driving component 51 on the rotation shaft 50 and/or the sliding block 62 is just a driving effect of the cutter 45 on the rotation shaft 50 and/or the sliding block 62. The first driving surface 511 is located at an upper inner edge of the proximal end of the driving groove 514. The end surface of the driving groove 514 may be of substantially triangular, trapezoidal or other irregular shape with rounded corners and is provided with a notch. The proximal end surface 513 may be located at a lower outer edge of the notch of the driving groove 514.

Referring to FIG. 23, the proximal end and the distal end of the connecting rod 63 may be further provided with a first pin hole 631 and a second pin hole 632, which are preferably round holes.

The sliding block 62 may be further provided with a main body 621 having an upper end surface 621a, a first pin shaft 622 and an abutting portion 623 having a distal end surface 623a. In a direction parallel with a bottom surface of the staple cartridge bracket 43 and perpendicular with the axial direction of the sliding block 62, the first pin shaft 622 and the abutting portion 623 are arranged at the distal end of the main body 621 in a staggered manner. The first pin shaft 622 cooperates with the first pin hole 631 of the connecting rod 63, and the first pin shaft 622 is preferably a cylindrical pin, such that the connecting rod 63 may pivotally rotate at the transverse side of the abutting portion 623 around the first pin shaft 622, that is, the abutting portion 623 cannot interfere with the movement of the connecting rod 63. When the sliding block 62 moves to a position below to the proximal end of the anvil 42, the upper end surface 621a of the main body 621 abuts against and supports the proximal end of the anvil 42 to apply a certain support force to the proximal end of the anvil 42, and this support force drives the anvil 42 to be closed towards the staple cartridge so as to assist the anvil 42 to be closed. When the cutter 45 is pulled to move from the distal end to the proximal end and restore, the distal end surface 623a may cooperate with the proximal end surface 513 of the cutter 45 for driving the sliding block 62 to move towards the proximal end and restore.

Figure 27:
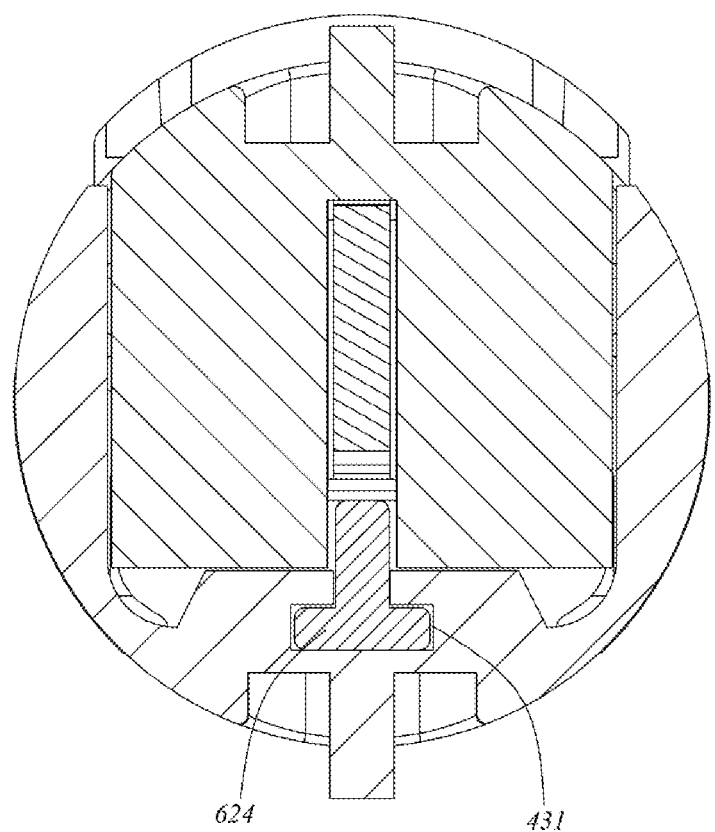
FIG. 27 is a sectional view along line C-C in FIG. 26A.

At the proximal end of the main body 621 of the sliding block 62 is provided a guiding portion 624, which as shown in FIG. 23 and FIG. 27, may be a guiding block extending from the proximal end of the main body 621 of the sliding block 62, and correspondingly, the staple cartridge bracket 43 may be provided with a guiding groove 431 cooperating with the guiding block. As an alternative embodiment, the guiding portion 624 may also be a guiding groove arranged in the sliding block 62, and correspondingly, the staple cartridge bracket 43 may be provided with a guiding block (not shown) cooperating with the guiding groove. A movement route of the sliding block 62 is defined by defining a movement route of the guiding portion 624, which facilitates the movement and restoration of the sliding block 62 along a set route. As can be seen from FIG. 24, the guiding portion 624 and the abutting portion 623 substantially overlap with the center axis of the rotation shaft 50 and of the cutter 45, and the connecting rod 63 is biased at a side of the center axis in a parallel manner.

Transverse outer ends of the first and second side wheels 5051 and 5052 of the rotation shaft 50 are pivotally connected to the staple cartridge bracket 43, such that the rotation shaft 50 may rotate relative to the staple cartridge bracket 43. Transverse inner ends of the first and second side wheels 5051 and 5052 are connected by the driving shaft 504. The driving shaft 504 is rotatably accommodated in the driving groove 514 of the cutter 45. When the cutter 45 moves towards the distal end under the action of the cutter push rod 47, the first driving surface 511 of the driving component 51 can drive the driving shaft 504 to move. Since the rotation shaft 50 is pivotally connected to the staple cartridge bracket 43 via the first and second side wheels 5051 and 5052, the driving shaft 504 is driven by the first driving surface 511 of the driving component 51 to rotate relative to the staple cartridge bracket 43, and at the same time, the driving shaft 504 drives the rotation shaft 50 to rotate entirely, and further drives the sliding block 62 to move towards the distal end via the connecting rod 63.

As a preferred solution, in an original status, that is, the staple cartridge assembly 40 of the stapler is in a to-be-fired status, the proximal end surface 513 of the cutter 45 is located at the proximal end of the staple cartridge bracket 43, and the driving shaft 504 is accommodated in the driving groove 514 of the cutter 45. But, the first driving surface 511 does not contact the driving shaft 504, and has a certain distance therefrom. Of course, the first driving surface 511 may also contact the driving shaft 504, but there is no interaction force therebetween. In the present invention, a section of the rotation shaft 504 may be, for example, set as a D-shaped, triangular, circular, rectangular, square or of an irregular shape, which will not be limited in the present invention.

The second pin shaft 506 is located on the second side wheel 5052 and can correspondingly move as the entire rotation of the rotation shaft 50, and an axial direction of the second pin shaft 506 is parallel with a transverse direction of the staple cartridge bracket 43. The second pin shaft 506 which is preferably a cylindrical pin cooperates with the second pin hole 632 of the connecting rod 63, and due to the above-mentioned cooperation, the sliding block 62 is connected to the rotation shaft 50. The second side wheel 5052 includes an accommodating space for receiving the second pin shaft 50 and the connecting rod 63. When the rotation shaft 50 rotates, the accommodating space can provide sufficient pivoting space in which the connecting rod 63 rotates around the second pin shaft 506. In the second embodiment, as shown in FIG. 23, the accommodating space is a tangent plane which connects the second pin shaft 506 and is perpendicular with the axial direction of the second pin shaft 506. As another alternative embodiment, the accommodating space may also be a groove (not shown) which connects the second pin shaft 506 and can provide a mounting space and a pivoting space for the connecting rod 63.

A side (at a position below the driving shaft 504 in FIG. 23) of the driving shaft 504 away from the second pin shaft 506 may be further provided with a containing groove 507 for accommodating the abutting portion 623 of the sliding block 62 or a structure below the driving groove 514 of the cutter 45. When the rotation shaft 50 rotates and drives the sliding block 62 to move towards the distal end, or the cutter 45 moves towards the proximal end to return to its original position, the abutting portion 623 of the sliding block 62 and the structure below the driving groove 514 of the cutter 45 can pass through the containing groove 507 so as to prevent the abutting portion 623 and the structure below the driving groove 514 from interfering with the movement of the driving shaft 504.

In the second embodiment, when the cutter push rod 47 drives the cutter 45 to move towards the distal end, the first driving surface 511 of the driving component 51 cooperates with the driving shaft 504 of the rotation shaft 50 and drives the rotation shaft 50 to rotate for a certain angle, for example, a maximum rotation angle in the clockwise direction is about 45 degrees to 150 degrees. In the present embodiment, the maximum rotation angle of the rotation shaft 50 is 130 degrees. The sliding block 62 is driven by the connecting rod 63 to slide towards the distal end, such that the upper end surface 621a of the main body 621 of the sliding block 62 gradually moves to a position below the proximal end of the anvil 42. Specifically, with respect to the angle as shown in the drawings, the first driving surface 511 drives the driving shaft 504 to rotate the rotation shaft 50 in the clockwise direction while the second pin shaft 506 drives the sliding block 62 to move towards the distal end via the connecting rod 63. The upper end surface 621a of the sliding block 62 gradually moves to a position below the proximal end of the anvil 42. In this process, the structure below the driving groove 514 of the cutter 45 gradually moves towards the distal end and exits from the containing groove 507 of the rotation shaft 50, while the abutting portion 623 of the sliding block 62 gradually moves towards the distal end and approaches the containing groove 507 of the rotation shaft 50. As another alternative embodiment, according to a position on the driving groove 514 of the cutter 45 where the first driving surface 511 of the cutter is located, if the first driving surface 511 is arranged at the lower inner edge of the proximal end of the driving groove 514, the rotation shaft 50 can also rotate in the anticlockwise direction.

Under the driving of the first driving surface 511 of the driving component 51, the driving shaft 504 rotates relative to the staple cartridge bracket 43. The first driving surface 511 of the driving component 51 is gradually staggered with the driving shaft 504 of the rotation shaft 50 in a vertical direction. The driving shaft 504 can move to the notch of the driving groove 514, and the first driving surface 511 at this moment cannot continue to drive the driving shaft 504. The cutter 54 continues to move towards the distal end, such that the cutter 45 is detached from the rotation shaft 50, the rotation shaft 50 stops rotating, and the cutter 45 continues to move towards the distal end till the suturing and cutting process is finished.

When the cutter 45 moves towards the proximal end to return to its original position, the proximal end surface 513 of the cutter 45 contacts the distal end surface 623a of the sliding block 62, such that the sliding block 62 is pushed to restore towards the proximal end and to drive the rotation shaft 50 to rotate inversely to return to its original position via the connecting rod 63. In this process, the abutting portion 623 of the sliding block 62 gradually moves towards the proximal end and away from the containing groove 507 of the rotation shaft 50, while the structure below the driving groove 514 in the cutter 45 gradually moves towards the proximal end and enters the containing groove 507 of the rotation shaft 50.

The use process of the staple cartridge assembly 40 of the present invention will be described in detail as below with reference to FIGS. 25 to 32. In the original status, as can be seen from local structures shown in part D and part E in FIGS. 26A and 26B, the anvil 42 is located above the staple cartridge bracket 43 and they are opened for a certain angle, and the auxiliary closing member is arranged at the proximal end of the staple cartridge bracket 43.

Figure 28A:
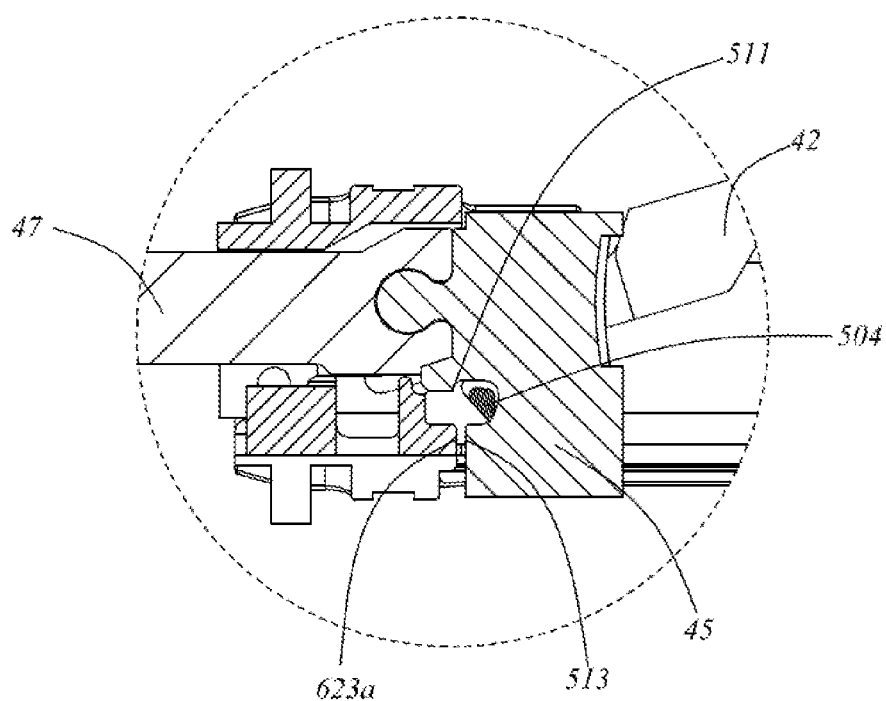
FIG. 28A is an enlarged view when a part D in FIG. 26A is in an original status.
Figure 28B:
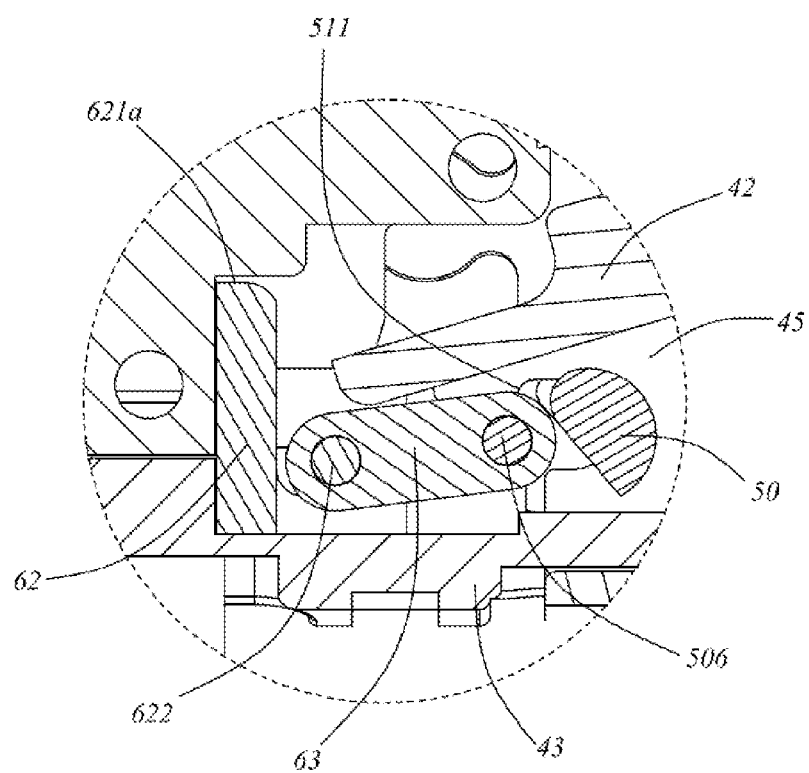
FIG. 28B is an enlarged view when a part E in FIG. 26B is in an original status.

As shown in FIGS. 28A and 28B, in an original status, the first driving surface 511 of the driving component 51 may not contact the driving shaft 504 of the rotation shaft 50 and is spaced therefrom for a certain distance, the rotation shaft 50 cannot rotate, and the sliding block 62 is arranged at the proximal end of the staple cartridge bracket 43. As the cutter push rod 47 pushes the cutter 45 to move towards the distal end, the anvil 42 is gradually closed by the action of the cutter 45, and the proximal end of the anvil 42 is gradually lifted.

Figure 29A:
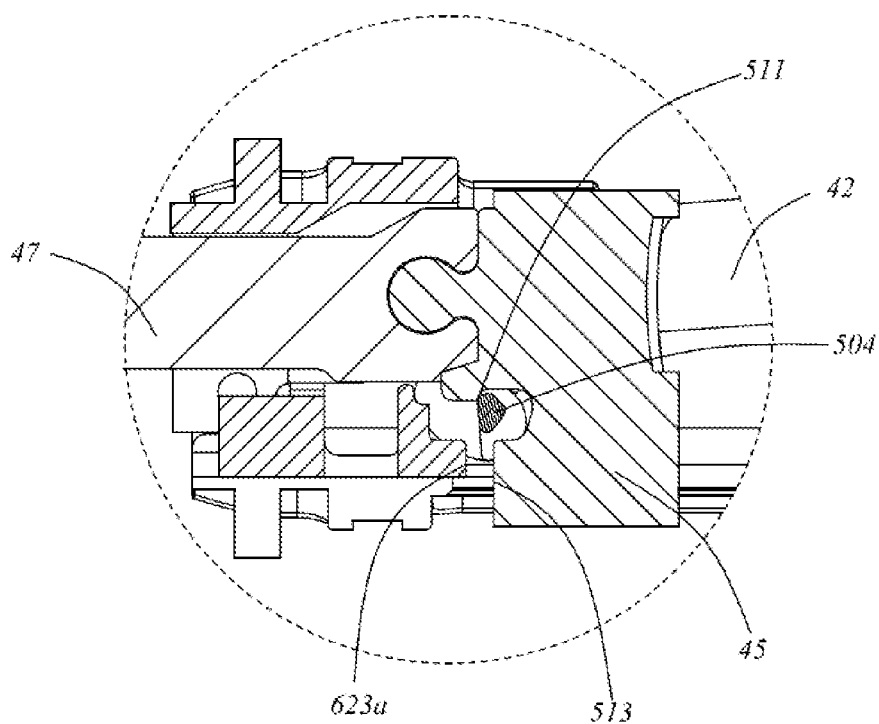
FIG. 29A is an enlarged view when the part D in FIG. 26A is in a second status.
Figure 29B:
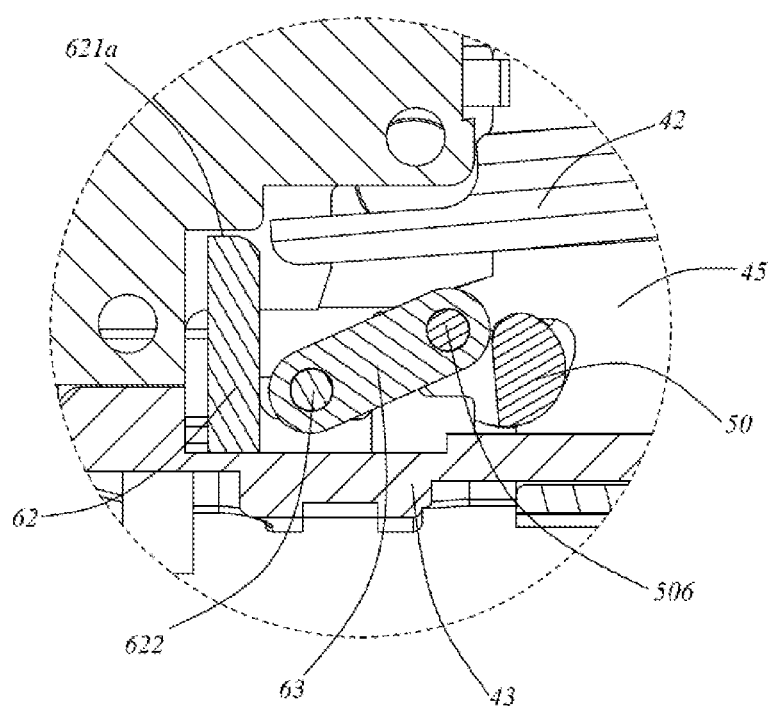
FIG. 29B is an enlarged view when the part E in FIG. 26B is in a second status.

As shown in FIGS. 29A and 29B, when the cutter 45 moves a certain distance towards the distal end, the first driving surface 511 of the driving component 51 contacts the driving shaft 504 of the rotation shaft 50 to enter a second status. As shown in FIG. 29A, the distal end surface 623a of the sliding block 62 is spaced from the proximal end surface 513 of the cutter 45 for a certain distance as the cutter 45 moves towards the distal end. When the cutter push rod 47 at this moment pushes the cutter 45 to continue to move towards the distal end, the first driving surface 511 drives the driving shaft 504 to rotate in the clockwise direction, the rotation shaft 50 is driven by the driving shaft 504 to begin to rotate, the second pin shaft 506 drives the sliding block 62 to move towards the distal end via the connecting rod 63 along the guiding groove 431 of the staple cartridge bracket 43, and meanwhile, the anvil 42 is gradually closed, and the proximal end of the anvil 42 is further warped upwards, as shown in FIG. 29.

Figure 30A:
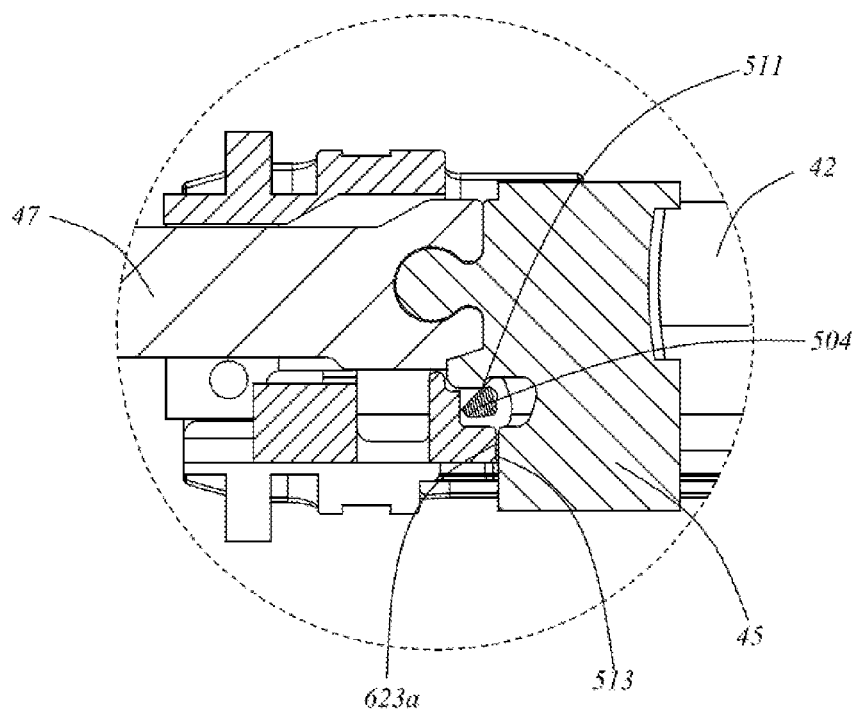
FIG. 30A is an enlarged view when the part D in FIG. 26A is in a third status.
Figure 30B:
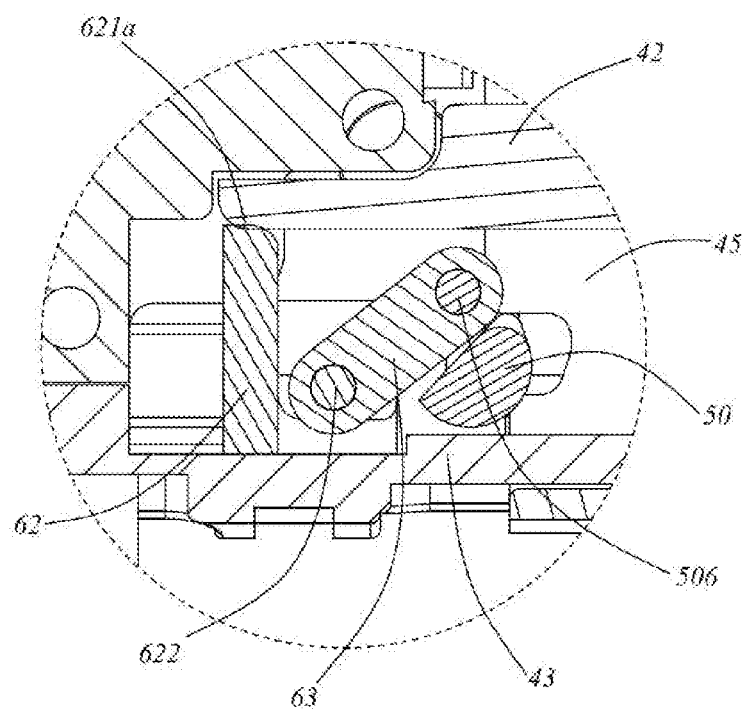
FIG. 30B is an enlarged view when the part E in FIG. 26B is in a third status.

As the cutter 45 continues to move further towards the distal end and, as shown in FIGS. 30A and 30B, enters a third status, after the first driving surface 511 of the driving component 51 pushes the rotation shaft 50 to rotate for an another certain angle, the sliding block 62 further moves another distance towards the distal end under the driving of the connecting rod 63, and the upper end surface 621a of the sliding block 62 gradually enters a position below the proximal end of the anvil 42 to support the proximal end of the anvil 42 and assist the anvil 42 to be closed. At the same time, due to the movement of the sliding block 62, the distal end surface 623a thereof substantially contacts the proximal end surface 513 of the cutter 45.

Figure 31A:
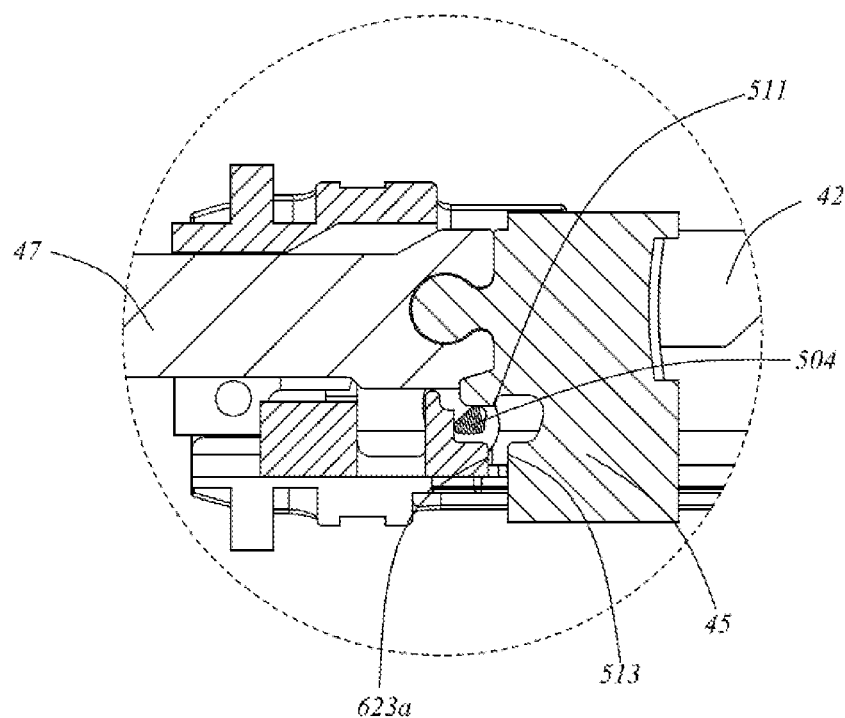
FIG. 31A is an enlarged view when the part D in FIG. 26A is in a fourth status.
Figure 31B:
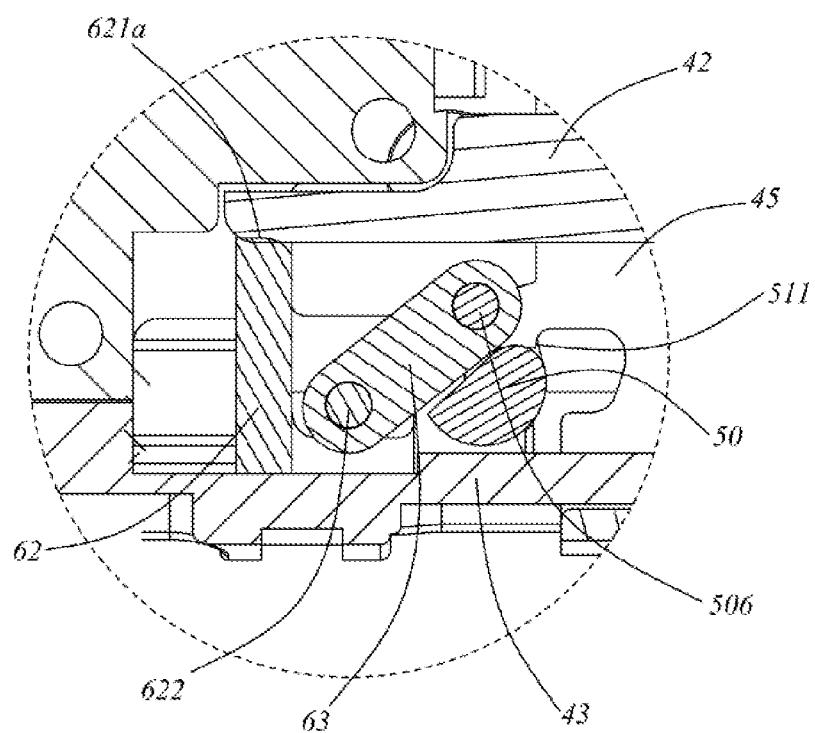
FIG. 31B is an enlarged view when the part E in FIG. 26B is in a forth status.

When the cutter 45 continues to move towards the distal end and, as shown in FIGS. 31A and 31B, enters a fourth status, the rotation shaft 50 at this moment has rotated for about 120 degrees with respect to the original status. The driving shaft 504 further rotates, and the first driving surface 511 of the driving component 51 is staggered with the driving shaft 504 of the rotation shaft 50 in a vertical direction. The driving shaft 504 moves to the notch of the driving groove 514 and is gradually detached from the driving groove 514, and the driving component 51 at this moment cannot continue to push the rotation shaft 50 to rotate, but the cutter 45 can continue to move towards the distal end to perform firing till the suturing and cutting process is finished. At the same time, the distal end surface 623a of the sliding block 62 is re-detached from the proximal end surface 513 of the cutter 45 with the distance therebetween increasing, the rotation shaft 50 stops moving at this angle while the sliding block 62 also moves towards the distal end to reach a maximum stroke and then stops moving. The upper end surface 621a of the sliding block 62 acts as a support for the proximal end of the anvil 42 during the cutting process of suturing and cutting, especially thick tissues by the cutter 45, to assist the anvil 42 to be closed, increase the clamping force and decrease the force applied to the cutter 45.

Figure 32:
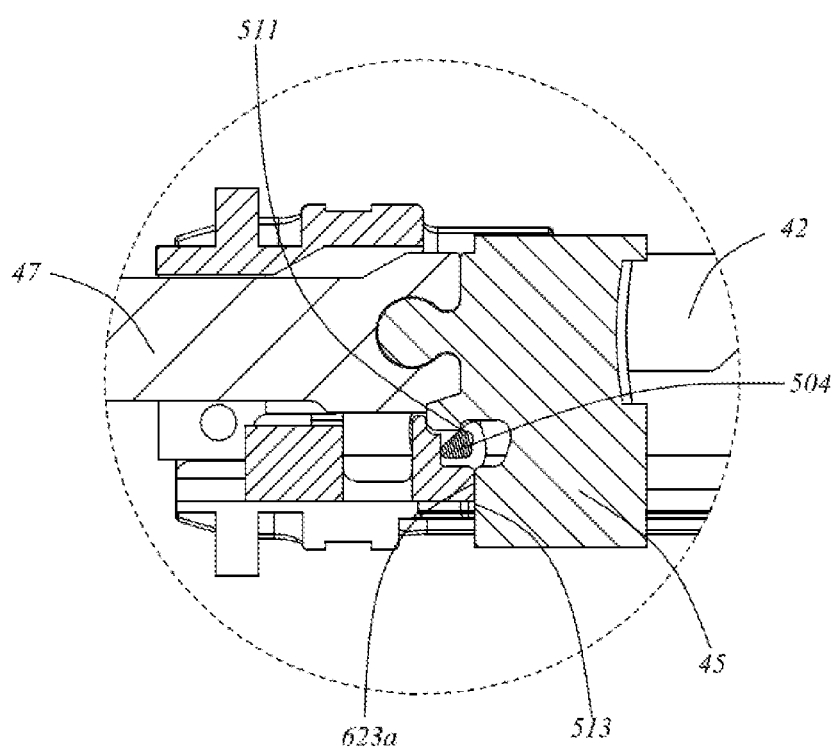
FIG. 32 is an enlarged view when the part D in FIG. 26A returns to its original position.

As shown in FIG. 32, after the firing process of the instrument is finished, when the cutter 45 is pulled to restore towards the proximal end, the proximal end surface 513 of the cutter 45 first touches the distal end surface 623a of the sliding block 62 as shown in FIG. 32, such that the sliding block 62 moves towards the proximal end to restore and drives the rotation shaft 50 to pivotally rotate towards the opposite direction via the connecting rod 63. The driving shaft 504 of the rotation shaft 50 finally passes through the notch of the driving groove 514 and enters a working position in the original status to finish the restoration of the rotation shaft 50.

In the second embodiment of the present invention, when the cutter 45 moves towards the distal end, the first driving surface 511 can drive the rotation shaft 50 to rotate and drive the sliding block 62 to move towards the distal end, till the sliding block 62 reaches a position of supporting the anvil 42, and then the rotation shaft 50 stops rotating and is detached from the cutter 45. When the cutter 45 is pulled back after the firing process is finished, the proximal end surface 513 of the cutter 45 can drive the sliding block 62 and the rotation shaft 50 to restore. Due to the above devices, the anvil is assisted to be closed, such that the force applied to the cutter 45 is decreased, and the operation risk is reduced.

The staple cartridge assembly 40 of the stapler of the present invention may be used in products such as endoscopic staplers and linear staplers of different specifications and types including, but not limited to, the staplers having cutting lengths of 55 mm, 60 mm, 75 mm, 80 mm, 100 mm, 120 mm and 150 mm.

It should be understood that although the description is described according to the above embodiments, each embodiment may not only include one independent technical solution. The presentation manner of the description is only for the sake of clarity. Those skilled in the art should take the description as an integral part. The technical solutions of the respective embodiments may be combined properly to form other embodiments understandable by those skilled in the art.

The above detailed description only illustrates the feasible embodiments of the present invention, and is not intended to limit the protection scope of the present invention. Equivalent embodiments or modifications within the scope and spirit of the present invention shall be embraced by the protection scope of the present invention.

The invention claimed is:

1. A staple cartridge assembly comprising a staple cartridge, an anvil and a cutter, wherein the cutter comprises a first end and a second end; the staple cartridge assembly also comprises a rotation shaft and an auxiliary closing member which is connected with the rotation shaft;
   the staple cartridge assembly is also provided with a driving component capable of driving the rotation shaft to rotate; the driving component and the cutter being integral; the cutter moves toward a distal end of the staple cartridge assembly and the driving component drives the rotation shaft to drive the auxiliary closing member to move in a process in which the staple cartridge assembly is converted from an original status to a closed status; when at least the staple cartridge assembly is in the closed status, one end surface of the auxiliary closing member abuts against the anvil to apply a force to the anvil for driving the anvil to be closed towards the staple cartridge, wherein
   the auxiliary closing member includes a cam rotatable around an axis of the rotation shaft;
   the driving component drives the rotation shaft to drive the cam to rotate in the process in which the staple cartridge assembly is converted from the original status to the closed status; when at least the staple cartridge assembly is in the closed status, a cam surface of the cam abuts against the anvil to apply a force to the anvil for driving the anvil to be closed towards the staple cartridge; and
   during a process of firing the staple cartridge assembly, the cutter moves towards the distal end of the staple cartridge assembly, and the driving component is detached from the rotation shaft and the rotation shaft becomes stationary after the driving component is detached from the rotation shaft.

2. The staple cartridge assembly of claim 1, wherein during a process of returning to the original status of the staple cartridge assembly after being fired, the cutter moves from the distal end of the staple cartridge assembly towards a proximal end thereof, and the driving component drives the rotation shaft to drive the cam to rotate such that the cam surface is detached from the anvil.

3. The staple cartridge assembly of claim 1, further comprising a staple cartridge bracket, a connector and an adapter, wherein the staple cartridge is detachably connected to the staple cartridge bracket, the connector is located at a proximal end of the staple cartridge bracket, and the adapter is connected to the connector and the staple cartridge bracket; and
   wherein the adapter cooperates with the staple cartridge bracket to form an accommodating space in which the rotation shaft can rotate, in which at least part of the rotation shaft is arranged and which limits the rotation of the rotation shaft.

4. The staple cartridge assembly of claim 3, wherein the adapter includes a fixing portion to cooperate with the staple cartridge bracket; an end surface of the fixing portion, close to the staple cartridge bracket, is arranged as a first arced surface; a protrusion corresponding to the fixing portion extends on the staple cartridge bracket; an end surface of the protrusion, close to the fixing portion, is arranged as a second arced surface; and the first and second arced surfaces together define the accommodating space.

5. The staple cartridge assembly of claim 1, wherein the anvil includes a cutter receiving groove to allow the cutter to pass; and the cam of the staple cartridge assembly includes two cams located at both sides of a cutting part of the cutter respectively and capable of contacting the anvil at both sides of the cutter receiving groove respectively.

6. A staple cartridge assembly comprising a staple cartridge, an anvil and a cutter, wherein the cutter comprises a first end and a second end; the staple cartridge assembly also comprises a rotation shaft and an auxiliary closing member which is connected with the rotation shaft;

the staple cartridge assembly is also provided with a driving component capable of driving the rotation shaft to rotate; the driving component and the cutter being integral; the cutter moves toward a distal end of the staple cartridge assembly and the driving component drives the rotation shaft to drive the auxiliary closing member to move in a process in which the staple cartridge assembly is converted from an original status to a closed status; when at least the staple cartridge assembly is in the closed status, one end surface of the auxiliary closing member abuts against the anvil to apply a force to the anvil for driving the anvil to be closed towards the staple cartridge, wherein the auxiliary closing member includes a cam rotatable around an axis of the rotation shaft;

the driving component drives the rotation shaft to drive the cam to rotate in the process in which the staple cartridge assembly is converted from the original status to the closed status; when at least the staple cartridge assembly is in the closed status, a cam surface of the cam abuts against the anvil to apply a force to the anvil for driving the anvil to be closed towards the staple cartridge; and the driving component includes a first driving surface and a second driving surface; during the process in which the staple cartridge assembly is converted from the original status to the closed status, the first driving surface drives the rotation shaft to rotate in a first direction; during a process of returning to the original status of the staple cartridge assembly after being fired, the second driving surface drives the rotation shaft to rotate in a second direction which is opposite to the first direction.

7. The staple cartridge assembly of claim 6, wherein the rotation shaft includes a concave portion, a contact portion and a convex portion; in the process in which the staple cartridge assembly is converted from the original status to the closed status, the first driving surface approaches and contacts the contact portion to drive the rotation shaft to rotate in the first direction; in a firing process of the staple cartridge assembly, the driving component is detached from the rotation shaft; during the process of returning to the original status of the staple cartridge assembly after being fired, the second driving surface approaches and contacts the convex portion to drive the rotation shaft to rotate in the second direction.

8. A staple cartridge assembly comprising a staple cartridge, an anvil and a cutter, wherein the cutter comprises a first end and a second end; the staple cartridge assembly also comprises a rotation shaft and an auxiliary closing member which is connected with the rotation shaft;

the staple cartridge assembly is also provided with a driving component capable of driving the rotation shaft to rotate; the driving component and the cutter being integral; the cutter moves toward a distal end of the staple cartridge assembly and the driving component drives the rotation shaft to drive the auxiliary closing member to move in a process in which the staple cartridge assembly is converted from an original status to a closed status; when at least the staple cartridge assembly is in the closed status, one end surface of the auxiliary closing member abuts against the anvil to apply a force to the anvil for driving the anvil to be closed towards the staple cartridge, the staple cartridge assembly further comprising:

a staple cartridge bracket for detachably accommodating the staple cartridge; and a cutter push rod for driving the cutter to move, wherein the auxiliary closing member is movably arranged in the staple cartridge bracket, and includes a sliding block and a connecting rod; the rotation shaft is pivotally connected to the staple cartridge bracket, and is rotatable relative thereto; two ends of the connecting rod are pivotally connected to the sliding block and the rotation shaft respectively;

when the cutter push rod drives the cutter to move from an original position towards a distal end of the staple cartridge, the driving component drives the rotation shaft in a first direction to rotate from an original position and drives the sliding block via the connecting rod, such that the sliding block moves from an original position to a position below a proximal end of the anvil;

when the cutter moves to a proximal end of the staple cartridge assembly to return to its original position, the driving component drives the sliding block to move towards the proximal end of the staple cartridge assembly to return to its original position, and drives the rotation shaft to rotate in a second direction opposite of the first direction to return to its original position via the connecting rod.

9. The staple cartridge assembly of claim 8, wherein the driving component includes a first driving surface, a proximal end surface and a driving groove, which are all arranged on the cutter; the first driving surface is located at an upper inner edge of a proximal end of the driving groove; the proximal end surface is located at a lower outer edge of the driving groove.

10. The staple cartridge assembly of claim 9, wherein one end of the connecting rod is provided with a first pin hole, and the other end thereof with a second pin hole;

the sliding block includes a main body having an upper end surface, a first pin shaft and an abutting portion having a distal end surface; the first pin shaft cooperates with the first pin hole of the connecting rod; the distal end surface of the abutting portion can cooperate with a proximal end surface of the cutter for restoring the sliding block.

11. The staple cartridge assembly of claim 10, wherein at a proximal end of the main body of the sliding block is provided a guiding portion, which is a guiding block extending from the proximal end of the main body of the sliding block or a guiding groove arranged in the sliding block.

12. The staple cartridge assembly of claim 10, wherein the rotation shaft includes a second pin shaft, a driving shaft, a first side wheel and a second side wheel; the second pin shaft cooperates with the second pin hole of the connecting rod; transverse outer ends of the first and second side wheels are pivotally connected to the staple cartridge bracket; transverse inner ends of the first and second side wheels are connected by the driving shaft;

when the cutter push rod drives the cutter to move towards the distal end, a first driving surface of the cutter cooperates with the driving shaft of the rotation shaft to rotate the rotation shaft in the first direction and to drive the sliding block via the connecting rod, such that the upper end surface of the main body of the sliding block moves to a position below the proximal end of the anvil; when the rotation shaft rotates for a certain angle, a location of the first driving surface of the cutter is staggered with a location of the driving shaft of the rotation shaft in the vertical direction, such that the cutter is detached from the rotation shaft, the rotation shaft stops rotating, and the cutter continues to move towards the distal end;

when the cutter moves towards the proximal end of the staple cartridge assembly to return to its original position, the proximal end surface of the cutter contacts the distal end surface of the sliding block, such that the sliding block is pushed in the direction of the proximal end of the staple cartridge assembly, and the rotation shaft is driven to rotate in the second direction to return to its original position via the connecting rod.

13. The staple cartridge assembly of claim 12, wherein the second pin shaft of the rotation shaft is located at the second side wheel; an axial direction of the second pin shaft is parallel with a transverse direction of the staple cartridge bracket; the second side wheel includes an accommodating space for receiving the second pin shaft and the connecting rod; when the rotation shaft rotates, the accommodating space can provide sufficient pivoting space in which the connecting rod rotates around the second pin shaft.

14. The staple cartridge assembly of claim 12, wherein a side of the driving shaft away from the second pin shaft is provided with a containing groove for receiving a structure below the driving groove of the cutter.

15. A medical stapler including the staple cartridge assembly of claim 8.

16. The medical stapler of claim 15, wherein the auxiliary closing member includes a cam rotatable around an axis of the rotation shaft; and the driving component drives the rotation shaft to drive the cam to rotate in the process in which the staple cartridge assembly is converted from the original status to the closed status; when at least the staple cartridge assembly is in the closed status, a cam surface of the cam abuts against the anvil to apply a force to the anvil for driving the anvil to be closed towards the staple cartridge.

17. The medical stapler of claim 16, wherein during a process of firing the staple cartridge assembly, the cutter moves towards the distal end of the staple cartridge assembly, and the driving component is detached from the rotation shaft and the rotation shaft becomes stationary after the driving component is detached from the rotation shaft.

18. The medical stapler of claim 16, wherein during a process of returning to the original status of the staple cartridge assembly after being fired, the cutter moves from the distal end of the staple cartridge assembly towards the proximal end thereof, and the driving component drives the rotation shaft to drive the cam to rotate such that the cam surface is detached from the anvil.

19. The medical stapler of claim 16, wherein the driving component includes a first driving surface and a second driving surface; during the process in which the staple cartridge assembly is converted from the original status to the closed status, the first driving surface drives the rotation shaft to rotate in a first direction; during a process of returning to the original status of the staple cartridge assembly after being fired, the second driving surface drives the rotation shaft to rotate in a second direction which is opposite to the first direction.

20. The medical stapler of claim 19, wherein the rotation shaft includes a concave portion, a contact portion and a convex portion; in the process in which the staple cartridge assembly is converted from the original status to the closed status, the first driving surface approaches and contacts the contact portion to drive the rotation shaft to rotate in the first direction; in a firing process of the staple cartridge assembly, the driving component is detached from the rotation shaft; during the process of returning to the original status of the staple cartridge assembly after being fired, the second driving surface approaches and contacts the convex portion to drive the rotation shaft to rotate in the second direction.

* * * * *